United States Patent
Bonnet

(10) Patent No.: US 9,255,118 B2
(45) Date of Patent: Feb. 9, 2016

(54) LIGHT INDUCED DRUG RELEASE

(75) Inventor: Sylvestre Bonnet, Leiden (NL)

(73) Assignee: UNIVERSITEIT LEIDEN, Leiden (NL)

( * ) Notice: Subject to any disclaimer, the term of this patent is extended or adjusted under 35 U.S.C. 154(b) by 356 days.

(21) Appl. No.: 13/880,253

(22) PCT Filed: Oct. 18, 2011

(86) PCT No.: PCT/IB2011/002479
§ 371 (c)(1),
(2), (4) Date: Jul. 1, 2013

(87) PCT Pub. No.: WO2012/052821
PCT Pub. Date: Apr. 26, 2012

(65) Prior Publication Data
US 2014/0148425 A1  May 29, 2014

(30) Foreign Application Priority Data
Oct. 18, 2010 (GB) .................................. 1017546.1

(51) Int. Cl.
*A61K 31/58* (2006.01)
*C07F 15/00* (2006.01)
*A61K 33/24* (2006.01)
*A61K 41/00* (2006.01)
*A61K 45/06* (2006.01)

(52) U.S. Cl.
CPC ............ *C07F 15/0053* (2013.01); *A61K 31/58* (2013.01); *A61K 33/24* (2013.01); *A61K 41/0042* (2013.01); *A61K 45/06* (2013.01)

(58) Field of Classification Search
CPC ............................ A61K 31/58; C07F 15/0053
USPC ......................................... 514/176, 188, 492
See application file for complete search history.

(56) References Cited

FOREIGN PATENT DOCUMENTS

WO     WO 93/09124     5/1993

OTHER PUBLICATIONS

Bligh, et al., "A Rapid Method of Total Lipid Extraction and Purification" Canadian Journal of Biochemistry and Physiology vol. 37, No. 8, Aug. 1959.
Bonnet, "Photochemical and Thermal Synthesis and Characterization of Polypyridine Ruthenium(II) Complexes Containing Different Monodentate Ligands" Dalton Trans., (2003) pp. 4654-4662, "First published as an Advance Article on the Web Nov. 10, 2003".
Bonnet, "Photochemical Expulsion of the Neutral Monodentate Ligand L in Ru(Terpy*)(Diimine)(L)2+: A Dramatic Effect of the Steric Properties of the Spectator Diimine Ligand" Inorganic Chemistry, (2004) vol. 43, No. 26, , pp. 8346-8354, "Published on Web Nov. 20, 2004".
Bonnet, "Synthesis and Photochemistry of a Two-Position Ru(terpy)(phen)(L)$^2$+ Scorpionate Complex" Inorganic Chemistry, (2006) vol. 45, No. 10 pp. 4024-4034, "Published on Web Apr. 21, 2006".
Bonnet, "Ruthenium-decorated lipid vesicles: Light-induced release of [Ru(terpy)(bpy)(OH2)]<2+> and thermal back coordination", Journal of the American Chemical Society, (2011) vol. 133 No. 2, pp. 252-261, "Published on Web Dec. 16, 2010".
Buil, et al., "Osmium-Alkenylcarbyne and—Akenylcarbene Complexes with an Steroid Skeleton: Formation of a Testosterone Organometallic Derivative Containing the 7H-Amino Adenine Tautomer" Organometallics (2009) vol. 28, pp. 5691-5696, "Published on Web Sep. 17, 2009".
Calvert. J.G.; Pitts, J.N., Chemical Actinometer for the Determination of Ultraviolet Light Intensities. In Photochemistry. Wiley and Sons: New York, 1967; pp. 780.
Collin, et al., "Ru(phen)$_2$(bis-thioether)$^2$+ Complexes: Synthesis and Photosubstitution Reactions" Inorganica Chimica Acta (2007) vol. 360 pp. 923-930, "Available online Jul. 6, 2006".
Corral, et al., "Ruthenium Polypyridyl Complexes and Their Modes of Interaction with DNA: Is there a Correlation Between These Interactions and the Antitumor Activity of the Compounds?" J Biol. Inorg. Chem. (2009) vol. 14 pp. 439-448, "Published online: Dec. 16, 2008".
Denk, et al., "Two-Photon Laser Scanning Fluorescence Microscopy" Science, (1990) vol. 248 pp. 73-76.
Denk, Two-Photon Scanning Photochemical Microscopy: Mapping Ligand-Gated Ion Channel Distributions: Proc. Natl. Acad. Jul. 1994 Sci. vol. 91, pp. 6629-6633.
Desai, et al., "New Steroid Haptens for Radioimmunoassay: Synthesis of Steroids Substituted with Thioether or Ester Linkages at the 2α-Position" Steroids, (1991) vol. 56 pp. 185-188.
Doyle, et al., "Cooperative Biinding at Lipid Bilayer Membrane Surfaces" Journal American Chemical Society, (2003) vol. 125, pp. 4593-4599 "Published on Web Mar. 21, 2003".
Hecker, et al., "Evidence for Dissociative Photosubstitution Reactions of [Ru(trpy)(bpy)(NCCH$_3$)]$^2$+. Crystal and Molecular Structure of [Ru(trpy)(bpy)](PF$_6$)x(CH$_3$)$_2$CO" Inorganic Chemistry (1991) vol. 30, pp. 659-666.
Hotze, et al., "New Cytotoxic and Water-Soluble Bis(2-Phenylazopyridine)ruthenium(II) Complexes" J. Med. Chem. (2003) vol. 46, pp. 1743-1750, "Published on Web Mar. 25, 2003".

(Continued)

*Primary Examiner* — Raymond Henley, III
(74) *Attorney, Agent, or Firm* — Hoxie & Associates LLC

(57) ABSTRACT

Photosensitive compounds for use in a method of treating a disease or condition are described. The photosensitive compounds have the formula R—Y, wherein R is a ruthenium complex and Y is at least one sulphur-containing photoreleasable group, and the compounds comprise at least one ruthenium-sulphur bond; or a pharmaceutically acceptable salt, solvate, ester or amide, such that upon influence of visible or near infra-red light (400-1400 nm) in vivo, said at least one ruthenium-sulphur bond is broken, thereby generating a pharmacologically active compound.

15 Claims, 3 Drawing Sheets

(56) References Cited

OTHER PUBLICATIONS

Jackson, et al., "Estrogen-Derived Steroidal Metal Complexes: Agents for Cellular Delivery of Metal Centers to Estrogen Receptor-Positive Cells" Inorganic Chemistry, (2001) vol. 40, pp. 3964-3973, "Published on Web Jul. 3, 2001".

Jaouen, et al., "Bioorganometallic Chemistry: A Future Direction for Transition Metal Organometallic Chemistry?" Acc. Chem. Res. (1993) vol. 26, pp. 361-369.

Jiang, et al., "Dynamic Molecular Recognition on the Surface of Vesicle Membranes" Chem. Commun. (2006) pp. 1407-1409, "First published as an Advance Article on the Web Feb. 20, 2006".

Laemmel, et al., Photosubstitution of Ancillary Ligands in Octahedral Mono-Terpyridine Ruthenium (II) Complexes, Cr. Acad. Sci. Paris (2000) vol. 3, pp. 43-49.

Lo, et al. "Non-Covalent Binding of Luminescent Transition Metal Polypyridine Complexes to Avidin, Indole-Binding Proteins and Estrogen Receptors" Coordination Chemistry Reviews (2007) vol. 251, pp. 2292-2310, "Available online Dec. 14, 2006".

Nikolenko, et al., "Two-Photon Uncaging of Neurochemicals Using Inorganic Metal Complexes" Chem. Commun. (2005) pp. 1752-1754, "Published as an advance article on the web Feb. 7, 2005".

Novakova, et al., "Correlation Between Cytotoxicity and DNA Binding of Polypyridyl Ruthenium Complexes" Biochemistry (1995) vol. 34, pp. 12369-12378.

Ossipov, et al., "Synthesis of the DNA-[Ru(tpy)(dppz)(CH$_3$CN)]$^{2+}$Conjugates and Their Photo Cross-Linking Studies with the Complementary DNA Strand" J. Am. Chem. Soc. (2002) vol. 124, pp. 13416-13433, "Published on web Oct. 22, 2002".

Reedijk "Metal-Ligand Exchange Kinetics in Platinum and Ruthenium Complexes" Platinum Metals Rev., (2008) vol. 52 (1), pp. 2-11.

Root, et al., "Synthesis and Characterization of (Bipyridine)(terpyridine)(chalcogenoether)ruthenium(II) Complexes. Kinetics and Mechanism of the Hydrogen Peroxide Oxidation of [(bpy)(tpy)RuS(CH$_3$)$_2$]$^{2+}$ to [(bpy)(tpy)RuS(O)(CH$_3$)$_2$]$^{2+}$. Kinetics of the Aquation of [(bpy)(tpy)RuS(O)(CH$_3$)$_2$]$^{2+1}$" Inorganic Chemistry, (1985) vol. 24, pp. 1464-1471.

Rouser, et al., "Two Dimensional Thin Layer Chromatographic Separation of -Polar Lipids and Determination of Phospholipids by Phosphorus Analysis of Spots" Lipids (1970) vol. 5, pp. 494-496.

Schobert, et al., "Steroid Conjugates of Dichloro(6-aminomethylnicotinate)platinum(II): Effects on DNA, Sec Hormone Binding Globulin, the Estrogen receptor, and Various Breast Cancer Cell Lines" Chem. Med. Chem. (2007) vol. 2, pp. 333-342.

Schofield, et al. "Potochemical and Thermal Ligand Exchange in a Ruthenium (II) Complex Based on a Scorpionate Terpyridine Ligand" Chem. Commun. (2003) pp. 188-189, "First Published as an advance article on the web Dec. 16, 2002".

Sheldrick, et al. "Synthesis and Stereochemistry of Diene-Ruthenium(II) Complexes of Sulphur-Containing α-amino Acids" Journal of Organometallic Chemistry, (1990) vol. 386 pp. 375-387.

Sigel, et al., "Metal Ion Complexes with Biotin and Biotin Derivatives. Participation of Sulfur in the Orientation of Divalent Cations" Biochemistry, (1969) vol. 8, No. 7, pp. 2687-2695.

Strickler, et al. " Three-dimensional Optical Data Storage in Refractive Media by Two-Photon Point Excitation" Optics Letters Nov. 15, 1991, Vo. 16 No. 22, pp. 1780-1782.

Takeuchi, et al., Redox and Spectral Properties of Monooxo Polypyridyl Complexes of Ruthenium and Osmium in Aqueous Media Inorganic Chemistry, 1984, vol. 23, pp. 1845-1851.

Witczak, et al., "Thiosugars: New Perspectives Regarding Availability and Potential Biochemical and Medicinal Applications" Appl. Microbiol. Biotechnol. (2005) vol. 69, pp. 237-244, "Published online: Oct. 21, 2005".

Clarke, Michael J. "Ruthenium Metallopharmaceuticals", Coordination Chemistry Reviews, 2002, vol. 232, pp. 69-93.

D'Hardemare, et al., "Design of Iron Chelators: Syntheses and Iron (III) Complexing Abilities of Tripodal Tris-Bidentate Ligands" Biometals, 2006, vol. 19, pp. 349-366.

Gianferrara, et al., "Ruthenium-Porphyrin Conjugates With Cytotoxic and Phototoxic Antitumor Activity" Journal of Medicinal Chemistry, 2010, vol. 53, No. 12, pp. 4678-4690.

Goldbach, et al., "N-Acetylmethionine and Biotin as Photocleavable Protective Groups of Ruthenium Polypyridyl Complexes" Chem. Eur. J., 2011, vol. 17, No. 36, pp. 9924-9929.

Smith, et al., "Targeted and Multifunctional Arene Ruthenium Chemotherapeutics" Dalton Transactions, 2011, vol. 40, pp. 10793-10800.

PCT/IB2011/002479 International Search Report and Written Opinion dated Mar. 15, 2012.

LIGHT INDUCED DRUG RELEASE

CROSS REFERENCE TO RELATED APPLICATIONS

This application is a United States National Stage Application under 35 U.S.C. 371 of PCT/IB2011/002479 filed on Oct. 18, 2011, which claims the benefit of GB 1017546.1, filed on Oct. 18, 2010, the contents of each of which are incorporated herein by reference in their entirety.

FIELD OF THE INVENTION

The present invention relates to the use of ruthenium-based compounds that are activated upon the influence of light to generate more biologically and/or pharmacologically active ruthenium compounds, as well as pharmaceutical agents, uses, and methods of treatments employing such compounds.

BACKGROUND TO THE INVENTION

Since the discovery of the cytotoxic activity of cisplatin in 1964, decades have been spent investigating the antitumor activity of platinum complexes. At the moment, cisplatin and its derivatives carboplatin and oxaliplatin belong to the most famous metal-based anticancer agents.[1]

Although very efficient, these cytostatic platinum complexes have severe drawbacks. First, resistance can occur, which is either intrinsic or acquired. Second, its antitumor activity is limited to only several tumor types. Third, the platinum complexes have a high general toxicity leading to negative side effects, including but not limited to kidney damage.

Although platinum anticancer agents are still the most commonly used metal-based anticancer drugs, their drawbacks have led scientists to investigate complexes of other platinum group metals, such as ruthenium. Ruthenium complexes with high cytotoxic activity can be divided into three classes. The first class contains the NAMI-based compounds. The second class are the organometallic half-sandwich compounds with the formula [Ru(η6-arene)(diamine)(Cl)]. The third class of compounds, which will be discussed in more detail, are ruthenium compounds with polypyridyl ligands.

Ruthenium complexes are thought to interact with biological ligands, and notably DNA. Since the ruthenium complexes have an octahedral instead of a square planar geometry, the binding modes to DNA probably differ from those of cytostatic platinum complexes. Furthermore, it has been shown that DNA is not the only target of several cytostatic ruthenium complexes, but that plasma proteins also bind to the metal centre.

One of the mechanisms of action of ruthenium-based anticancer compounds is thermal formation of an aqua ruthenium complex, which binds to DNA and proteins. Like for cisplatin DNA is one target of antitumor-active ruthenium complexes, but ruthenium-protein interactions play a significant role as well. (Messori, L.; Orioli, P.; Vullo, D., *Eur. J. Biochem.* 2000, 267, 1206; Ho, M.-Y.; Chiou, M.-L.; Du, W.-S.; Chang, F. Y.; Chen, Y.-H.; Weng, Y.-J.; Cheng, C.-C., *J. Inorg. Biochem.* 2011, 105, 902). Whatever the final target might be, the main mechanism of action of ruthenium-based anticancer drugs containing chloride ligands bound to the ruthenium center, [Ru—Cl], comprises: 1) hydrolysis of the metal-chloride bond, to give the aqua complex [Ru—OH$_2$], followed by 2) binding of the aqua complex to a biological target, to give a DNA- or protein-bound species; and finally 3) apoptosis triggered by these ruthenium adducts. Although hydrolysis of the Ru—Cl bond occurs faster inside the cells due to the lower cytoplasmic chloride concentration, it is a thermal process that can occur anywhere, which is one of the reasons for the general toxicity of ruthenium-based drugs.

Two examples of polypyridyl ruthenium compounds which show high cytostatic activity are mer-[Ru(terpy)(Cl)$_3$][2] and α-[Ru(azpy)$_2$(Cl)$_2$][3] Another known and interesting anticancer agent is [Ru(terpy)(apy)(Cl)](Cl).[4] It is believed that this compound is converted into the cationic active form [Ru(terpy)(apy)(H$_2$O)]$^{2+}$ in the body by thermal cleavage of the coordination bond between the ruthenium and the chlorine atoms. The structure of the biologically active form of this complex is shown below Scheme 1. Structure of the cytostatic agent [Ru(terpy)(apy)(H$_2$O)]$^{2+}$.

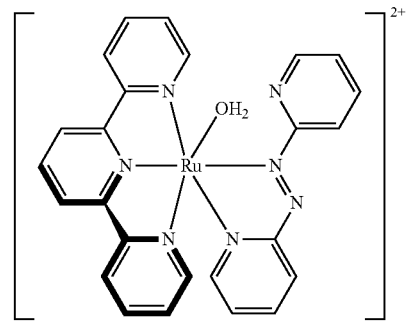

Since human body temperature is 37° C., the anticancer agent [Ru(terpy)(apy)(H$_2$O)]$^{2+}$ might be released anywhere in the body when [Ru(terpy)(apy)(Cl)](Cl) is used as a drug. This affects both healthy and tumor cells. Naturally an effect on healthy cells by a cytostatic agent causes unwanted side effects.

In addition, some of the biologically active polypyridyl ruthenium compounds, such as mer-[Ru(terpy)(Cl)$_3$] or α-[Ru(azpy)$_2$(Cl)$_2$], are poorly soluble in water, which limits their pharmaceutical use.

Tumor irradiation in vivo is clinically employed during photodynamic therapy (PDT). PDT consists in the administration of a photosensitizer (generally a porphyrin or phthalocyanine compound), followed by the non-invasive irradiation of the tumor(s) with light (Brown, S. B.; Brown, E. A.; Walker, I., *Lancet Oncol.* 2004, 5, 497). The photosensitizer is non-toxic in the dark, but in presence of oxygen and light it produces a significant amount of highly toxic, short-lived radical species, culminating in cell death via irreversible damage to cellular components such as proteins, lipids, and DNA.

Overall, using light to activate anticancer prodrugs is attractive in anticancer therapy as it is poorly invasive, spatially accurate, and as it can reach places where surgery is impossible. Of course drug activation by light is particularly suited for skin, lung, or digestive track cancers, for which a source of light can easily be directed onto the tumor. However, it is also possible to shine light on internal organs using endoscopy, to cure prostate, head and neck, bile duct, or bladder cancers for example. Several photosensitizers for PDT have been clinically approved, so that light irradiation techniques are now available within hospitals.

PDT is selective and highly effective in certain cancers. However, there are PDT-resistant tumors as well. The selectivity of PDT is high because: 1) the photosensitizer accumulates in tumor tissues; 2) the photochemically generated radical species are highly reactive, which limits oxidative damage to the vicinity of the photosensitizer; and 3) only the tumor is irradiated, which physically confines the photodynamic action to tumor tissues. Due to its selectivity, toxicity and patient discomfort are kept to a minimum, while PDT has proven to be highly efficacious in the treatment of various cancer types. However, several cancers, including recurrent superficial bladder cancer, non-resectable cholangiocarcinomas, and certain head-and-neck and esophageal cancers, respond poorly to PDT (Nseyo, U. O.; DeHaven, J.; Dougherty, T. J.; Potter, W. R.; Merrill, D. L.; Lundahl, S. L.; Lamm, D. L., *J. Clin. Laser Med. Surg.* 1998, 16, 61).

One of the reasons of such recalcitrance is the poor oxygenation of tumor tissues (Coleman, C. N., *J. Natl. Cancer Inst.* 1988, 80, 310; Mellor, H.; Snelling, S.; Hall, M.; Mdok, S.; Jaffar, M.; Hambley, T.; Callaghan, R., *Biochem. Pharmacol.* 2005, 70, 1137) which is a consequence of their poor vasculature and high demand in energy.

It is an object of the present invention to obviate and/or mitigate one or more of the aforementioned disadvantages.

It is an object of the present invention to provide ruthenium-based compounds, which are initially biologically inactive (or biologically inactive to a limited extent only) and that can be activated in due course through the influence of light to become biologically active or more biologically active.

SUMMARY OF THE INVENTION

In a first aspect there is provided photosensitive compound for use in a method of treating a disease or condition, said photosensitive compound having the formula R—Y, wherein R is a ruthenium complex and Y is at least one sulphur-containing photoreleasable group, and wherein the compound comprises at least one ruthenium-sulphur bond; or a pharmaceutically acceptable salt, solvate, ester or amide, such that upon influence of visible or near infra-red light (400-1400 nm) in vivo, said at least one ruthenium-sulphur bond is broken, thereby generating a pharmacologically active compound It is desired that the biological activity of the ruthenium compound R and/or that of the free group Y, is different/higher, than that of the initial ruthenium compound R—Y. It is to be appreciated that the ruthenium compound R and/or the free group Y may be the biologically active compounds. One advantage of the compounds according to the present invention is that the upon photocleavage, singlet oxygen does not require to be produced (unlike in PDT described in the background section) in order for the compounds to be active. Thus, in a preferred embodiment, the compounds of the present invention do not release singlet oxygen upon photoactivation.

Preferably the ruthenium complexes and compounds of the present invention comprise Ru(II).

Typically, the photo-releasable group Y is a sulfur-containing monodentate or bidentate ligand capable of coordinating to the Ru complex through at least one sulfur atom.

Sulfur-containing photoreleasable ligands are typically thioethers and sulfoxides. Examples of suitable thioether groups which are capable of forming at least one coordination bond(s) to the Ru complex include compounds based on biotin (FIG. 3), alkylcysteine (including methylcysteine), methionine, alkylated thiols, dimethylsulfide, phenylmethylsulfide, diphenylsulfide, dialkylsulfide, phenothiazine, and derivatives thereof such as chlorpromazine or promethazine. Alternatively, the thioether-based ligand might also be a methionine- or alkylcystein-containing polypeptide, or a thioether-containing organic molecule of natural origin, such as a biotin derivative, ranitidine, methyl coenzyme M, a thioether-containing sugar (e.g. 5-thio-D-mannose or 1,4-anhydro-4-thio-D-mannitol),[5] a thioether-containing steroid,[6] a thioether-containing beta lactam antibiotic (e.g. a penicillin or a cephalosporin), or a thio-analogue of an oxygen-based ether.

Polypeptides might naturally contain one or several sulfur-based amino acid such as methionine or methylcystein, or be artificially functionalized with one or several additional methionine or methylcystein group(s) in order to bind to ruthenium. Typically, such sulfur-containing polypeptide might be able to target selectively to the cancer cell (e.g., bombesin, or a methionine-derivated transferrin), the nucleus (e.g., a NLS conjugate), the cytoplasm (e.g., a TAT peptide), or the mitochondria (e.g., a MLS conjugate), in order to achieve selective delivery of the drug before light irradiation is applied. Thus, Y may consist in a protein coordinated to the Ru complex R via a sulphur atom, whether this sulphur atom is part of the protein structure (methionine, methylcystein, cysteine), or whether it has been covalently conjugated to the protein, for example via click chemistry, or via the formation of an amide or ester bond. These proteins may comprise cell-penetrating peptides, antibodies against specific epitopes on the cancer cell (e.g., transferrin receptor, epidermal growth factor receptor, etc.), their respective fragment antigen binding (fab) or Fc fragments. Alternatively, choline and glucose may be covalently functionalized with a thioether group Y for binding to the ruthenium complex R, as they are heavily needed by cancer cells and represent a potent cancer targeting fragment as well. Lastly, iminodiacetic acid derivatives such as mebrofenin and compounds such as indocyanine green are exclusively taken up by liver cells, particularly in hepatocellular carcinomas. Since these tumors don't have bile ducts, the compounds enter the cell and are retained there, as opposed to healthy hepatocytes, which clear these compounds through the biliary system. This phenomenon could be exploited for liver-specific tumors after conjugation of these compounds to Ru-complexes.

Examples of sulfoxide groups which are capable of forming at least one coordination bond(s) to the Ru complex include compounds based on dimethylsulfoxide (DMSO), phenylmethylsulfoxide, diphenylsulfoxide, alkylmethylsulfoxide or dialkylsulfoxide (where the alkyl chains are $C_nH_{2n+1}$, n=2-18), alliin, or any sulfoxide derivative of one of the thioethers specified above, including peptides containing sulfoxide groups.

For some of the aforementioned sulfur-containing ligands, another sulfur-, nitrogen- or oxygen-based functional group may be present, so that the ligand may coordinate in a bidentate fashion, thus doing two coordination bonds with one ruthenium center. For example, methionine can bind either as a monodentate ligand through its sulfur atom (such as in compound [Ru(terpy)(bpy)(methionine)](Cl)$_2$), or as a bidentate ligand through both the sulfur and nitrogen atom.[7] Photochemically breaking one or the two bonds of such bidentate ligands to release or increase the biological activity of the ruthenium compound is also the subject of this invention.

Preferred ligands may be based or derived from sulfur-containing natural molecules such as biotin, methylcysteine, methionine, phenothiazine, and their corresponding sulfoxides, linked or not to derivatives of cholesterol or lipids, examples of which are shown below:

Scheme 2. Preferred monodentate sulfur-containing ligands
Y, X = O or NH, R = H, Me, Et, Pr, Bu, cholesterol, cholestanol, or a lipid (such as cholesterol or phosphatidylethanolamine), R' = H, Ac, Boc, Fmoc.
Y = (monodentate thioether)
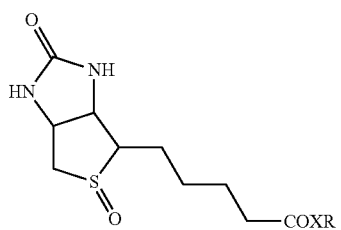
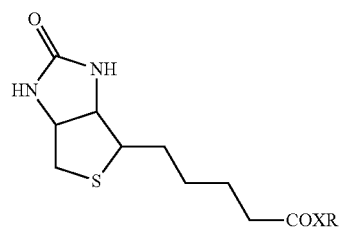
Biotin
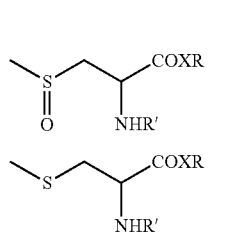
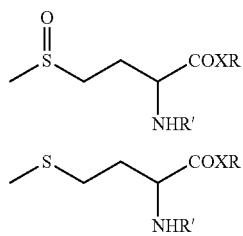
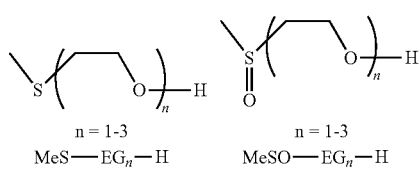
Me-cystein    Methionine    $n = 1-3$      $n = 1-3$
                            MeS—$EG_n$—H   MeSO—$EG_n$—H
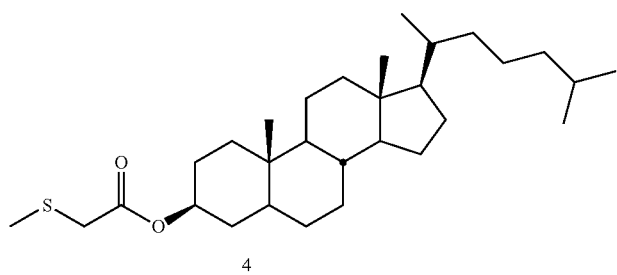
4
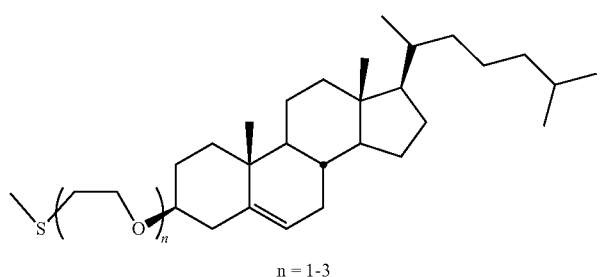
$n = 1-3$

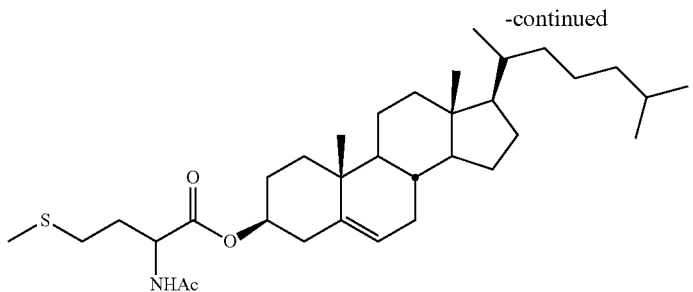

AMet-Chol

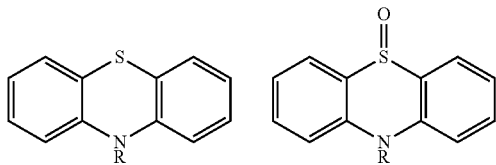

R-ptz

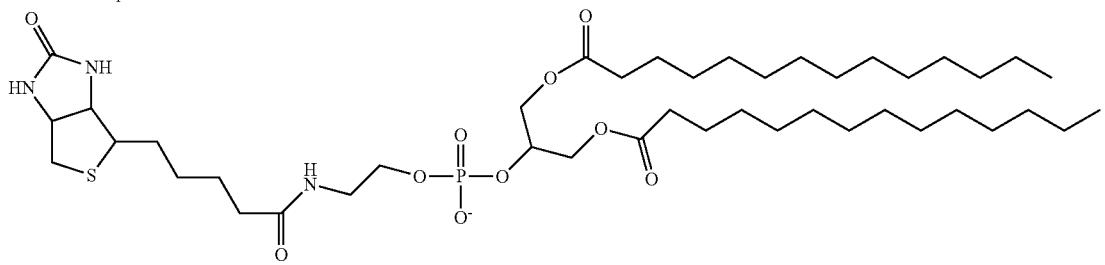

Biotin-DMPE

For ligands Y that comprise lipid derivatives it is understood that these may incorporate into lipid bilayers such as that forming liposomes. Thus, vesicles may be formed using neutral, zwitterionic, or charged lipids or surfactants as well known to a skilled addressee, and the photosensitive metal complex comprising a lipid moiety allowed to become part of the membrane structure. In general liposomes constitute an advantageous carrier system due to the facile preparation techniques (that allow bulk production), their manipulatable attributes, their water solubility, and their ability to encapsulate hydrophilic and lipophilic molecules at high efficiencies. In addition to the inherent non-toxicity of neutral phospholipids, the composition of liposomes can be modified to facilitate the unique prerequisites of a drug delivery system. For example, neutral DMPC liposomes functionalized at their surface by ruthenium polypyridyl complexes, are well taken up by cancer cells (see Example 7 and FIG. 4), so that such liposomes can be seen as a drug delivery system (DDS). The skilled addressee is further directed to "Liposomes—a practical approach" Second edition (2003) Edited by Vladimir P. Torchilin and Volkmar Weissig and R. R. Sawant & V. P. Torchilin, Soft Matter 2010, vol 6 (7), p 4026, for further teaching of how the compounds of the present invention may be combined/complexed with liposomes and related structures, in order to deliver the compounds to cells of choice, such as cancer cells.

Preferably, the head group of the lipids comprising the liposomal DDS is selected from the group consisting of: phosphocholine, phosphoethanolamine, phosphatidic acid, phosphoglycerol, phosphoserine, phosphoinositol, sphingosine, diglycerophosphate, glycerol, ethylene glycol, galloylglycerol, and glycero-3-succinate.

The acyl chain of the lipid is preferably selected from the group consisting of: tridecanoyl (13 carbons), myristoyl (14 carbons), myristoleoyl (14 carbons, cis-alkene at $\Delta_9$), myristelaidoyl (14 carbons, trans-alkene at $\Delta_9$), pentadecanoyl (15 carbons), palmitoyl (16 carbons), palmitoleoyl (16 carbons, cis-alkene at $\Delta_9$), palmitelaidoyl (16 carbons, trans-alkene at $\Delta_9$), phytanoyl (16 carbons, methylated at $\Delta_{3,7,11,15}$), heptadecanoyl (17 carbons), stearoyl (18 carbons), petroselinoyl (18 carbons, cis-alkene at $\Delta_6$), oleoyl (18 carbons, cis-alkene at $\Delta_9$), elaidoyl (18 carbons, trans-alkene at $\Delta_9$), linoleoyl (18 carbons, cis-alkenes at $\Delta_{9,12}$), linolenoyl (18 carbons, cis-alkenes at $\Delta_{9,12,15}$), nonadecanoyl (19 carbons), arachidoyl (20 carbons), eicosenoyl (20 carbons, cis-alkene at $\Delta_{11}$), arachidonoyl (20 carbons, cis-alkenes at $\Delta_{5,8,11,14}$), heniecosanoyl (21 carbons), behenoyl (22 carbons), erucoyl (22 carbons, cis-alkene at $\Delta_{13}$), docosahexaenoyl (22 carbons, cis-alkenes at $\Delta_{4,7,10,13,16,19}$), trucisanoyl (23 carbons), lignoceroyl (24 carbons), nervonoyl (24 carbons, cis-alkene at $\Delta_{15}$).

Enhancement of the in vivo circulation time of the liposome can be accomplished by proper sizing. The methods employed for sizing are well known by the skilled addressee, and for example described in Awasthi V D et al. Int J Pharm. 2003 Mar. 6; 253(1-2):121-32. Suitable liposomes for use as a drug delivery system of the invention have a size between 30 and 1500 nm, preferably between 90 and 200 nm [Liu D et al. Biochim Biophys Acta. 1992 Feb. 17; 1104(1):95-101], more preferably between 160 and 200 nm, and most preferably about 180 nm. In order to prevent liposome aggregation and fusion and to enhance circulatory half life, the liposomes may be sterically stabilized. Methods for sterical stabilization are for example described in [Klibanov A L et al. FEBS Lett.

1990 Jul. 30; 268(1):235-7, Senior J et al. Biochim Biophys Acta. 1991 Feb. 11; 1062(1):77-82, Allen T M et al. Biochim Biophys Acta. 1991 Jul. 1; 1066(1):29-36]. In a preferred embodiment this is achieved by the grafting of poly(ethylene glycol) (PEG, also referred to as polyethylene oxide (PEO) or polyoxyethylene (POE)) onto the liposomal surface as described in [Klibanov A L et al. FEBS Lett. 1990 Jul. 30; 268(1):235-7, Allen T M et al. Biochim Biophys Acta. 1991 Jul. 1; 1066(1):29-36, Blume G et al. Biochim Biophys Acta. 1990 Nov. 2; 1029(1):91-7]. This can be effected by including a molar fraction of linear or branched PEG [Torchilin V P et al. J Pharm Sci. 1995 September; 84(9):1049-53] covalently linked to a lipid constituent (usually phosphatidylethanolamine (PE) or phosphatidylglycerol (PG)) or to a hydrophobic anchor molecule in the lipid bilayer, such as, but not limited to, cholesterol, polypropylene oxide) (PPO), or mono- or diacyls. The presence of a "dense conformational cloud" by the PEG polymers over the liposome surface, the repulsive interactions between PEG-grafted membranes and blood constituents, the hydrophilicity of PEGylated formulations, and the decreased rate of plasma protein adsorption on the hydrophilic surface of PEGylated liposomes impose so-called 'stealth' properties through which rapid clearance by cells of the reticuloendothelial system is considerably forestalled. The use of these techniques for 'stealthing' is part of the present invention.

Finally, it is also envisaged that, next to being functionalized with the Ru—Y complexes and/or the PEGylate lipids, the surface of the liposome may also comprise cancer cell-targeting molecules, such as, for example, peptides, antibodies, glucose, or folate. These targeting molecules are expected to recognize specifically receptors overexpressed by certain types of cells, such as cancer cells and bind to it, thus increasing the selective delivery of the Ru—Y compound to the particular cell, before light activation.

It is also possible to photorelease bidentate ligands Y—Y, provided the coordination sphere of the ruthenium complex is crowded enough.[8] Then, two molecules of solvent replace the photoreleased ligand instead of one. Typically, Y—Y can be an amino acid such as methionine or methylcystein, which binds to ruthenium through two out of the three heteroatoms.[7] It can also be the sulfoxide derivative of methionine or methylcystein, which binds to ruthenium through both the N and S, or N and O, atoms. Alternatively, it can be a derivative of 2,2'-bipyridine or 1,10-phenanthroline, or a bisthioether, such as a Met-Met dipeptide. Finally, any of these bidentate ligands may be covalently functionalized with a lipid moiety, for attachment of the ruthenium complex at the surface of a liposome drug delivery system, and light-induced release after uptake of the liposome by the cancer cell.

The Ru complexes of the present invention may conform to the following structures:

Scheme 3. General structure of the ruthenium complexes that may be utilised in accordance with this invention.

A]

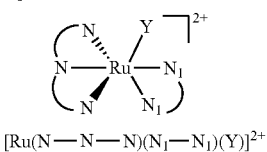

$[Ru(N\text{—}N\text{—}N)(N_1\text{—}N_1)(Y)]^{2+}$

-continued

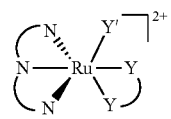

$[Ru(N\text{—}N\text{—}N)(Y\text{—}Y)(Y')]^{2+}$

B]

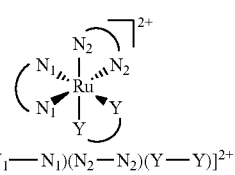

$[Ru(N_1\text{—}N_1)(N_2\text{—}N_2)(Y\text{—}Y)]^{2+}$

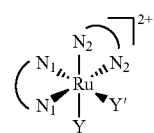

$[Ru(N_1\text{—}N_1)(N_2\text{—}N_2)(Y)(Y')]^{2+}$

C]

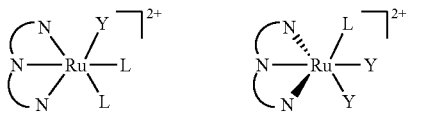

$[Ru(N\text{—}N\text{—}N)(L)_2(Y)]^{2+}$   $[Ru(N\text{—}N\text{—}N)(Y)_2(L)]^{2+}$

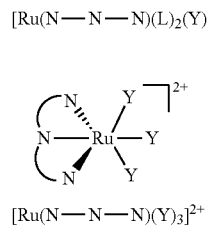

$[Ru(N\text{—}N\text{—}N)(Y)_3]^{2+}$

In complexes of group A and B, Y and Y' are monodentate sulfur-containing ligand that can be photoreleased, whereas the terdentate (N—N—N) or bidentate (N$_1$—N$_1$, N$_2$—N$_2$) chelates stay bound to ruthenium. In case Y and/or Y' may be covalently bound to a lipid moiety such as cholesterol or a phospholipid, cleavage of the ruthenium-sulfur bond may induce the detachment of the ruthenium complex from the lipid bilayer. Y—Y is a sulfur-containing bidentate ligand that can be photoreleased. Y and Y' may be the same or different monodentate sulfur-containing ligands mentioned above, and N$_1$—N$_1$ and N$_2$—N$_2$ are selected from one or more of the structures shown below, where R is a hydroxy, H, C$_1$-C$_4$ alkyl, carboxy, alkoxy, amino, N,N-dimethylamino, carbonyl, or nitro group. Alternatively, Y' may also be a monodentate ligand that is photochemically less labile than Y, such as pyridine or acetonitrile. Finally, in group C N—N—N is a terdentate chelate that stays bound to ruthenium whereas Y is a monodentate sulfur-based ligand that can be photoreleased and L are monodentate ligands that may be photochemically less labile than Y. Typically, L might be a substituted pyridine, or acetonitrile.

N—N—N may be a terdentate ligand of the following type (where R is a hydroxy, H, C$_1$-C$_4$ alkyl, carboxy, alkoxy, amino, N,N-dimethylamino, carbonyl, halide, or nitro group, and R' is H or an alkyl group):

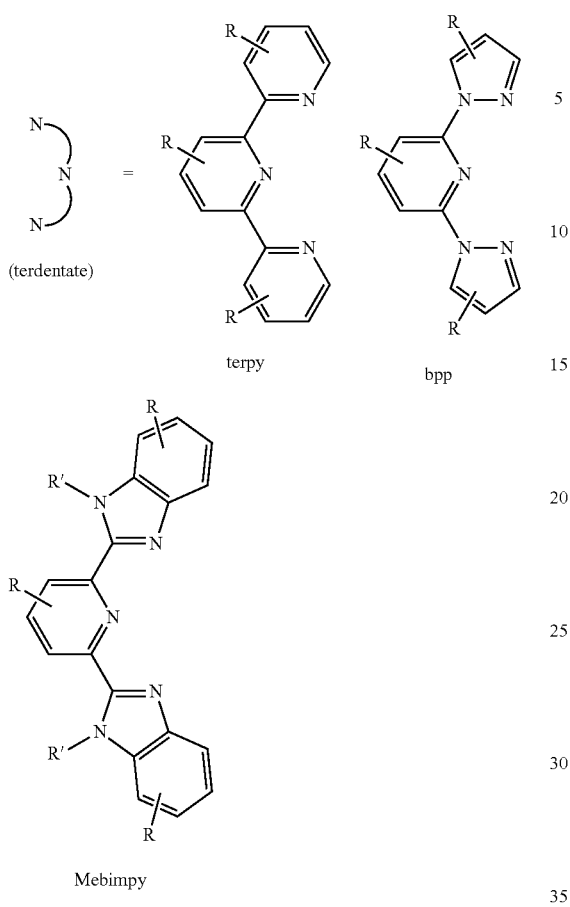
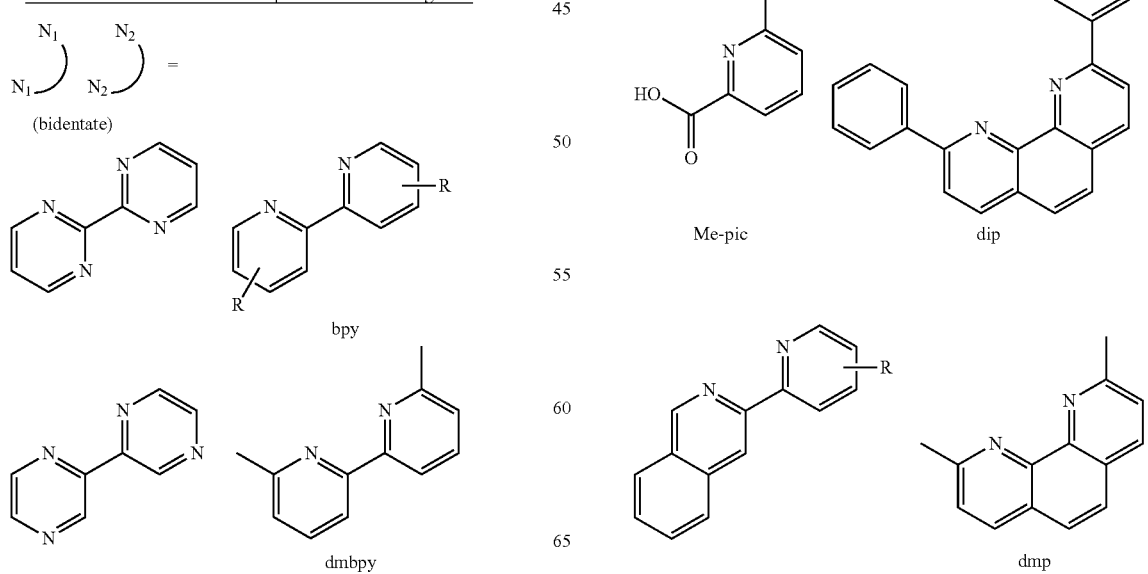
$N_1$—$N_1$, $N_2$—$N_2$ and Y—Y may be a bidentate ligands of the following type (where R is a hydroxy, H, $C_1$-$C_4$ alkyl, carboxy, alkoxy, amino, N,N-dimethylamino, carbonyl, halide, or nitro group and R'=H, Me, Et, Pr, Bu, halide, or a lipid for integration in a liposome carrier):

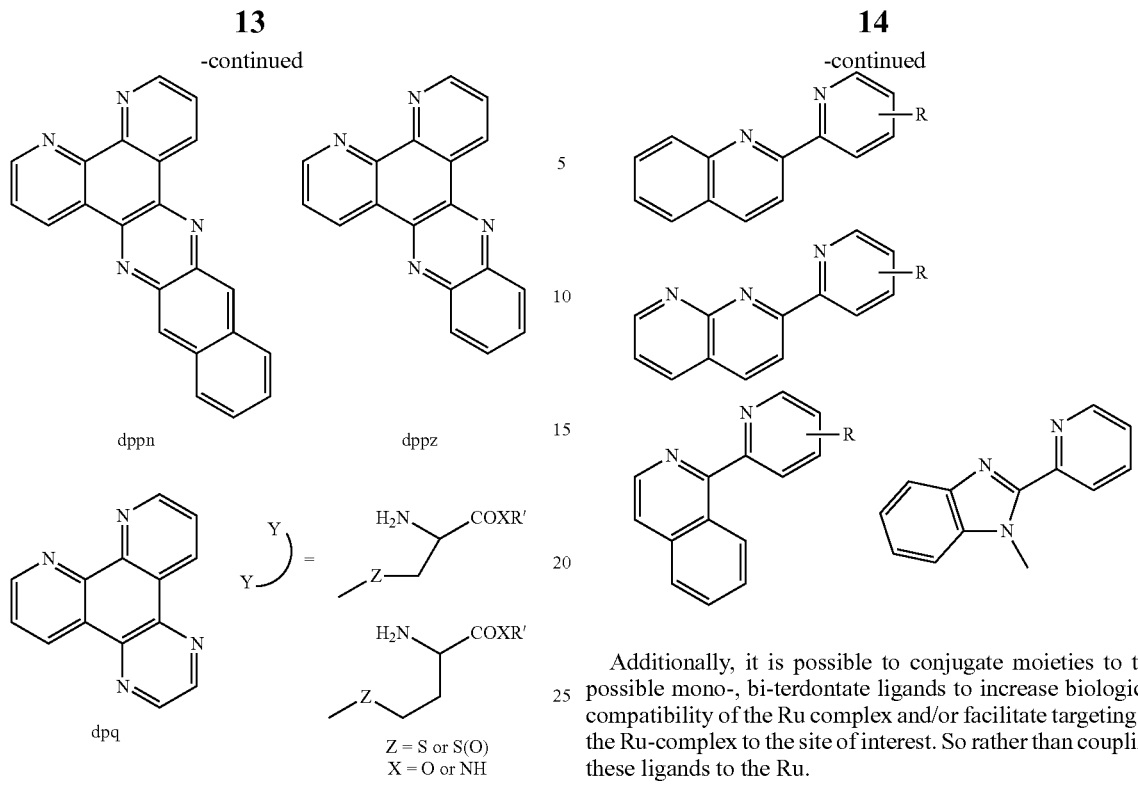

Additionally, it is possible to conjugate moieties to the possible mono-, bi-terdontate ligands to increase biological compatibility of the Ru complex and/or facilitate targeting of the Ru-complex to the site of interest. So rather than coupling these ligands to the Ru.

Most preferred compounds according to the present invention conform to the following structures:

Scheme 5. Most preferred structures; counter anions have been omitted.

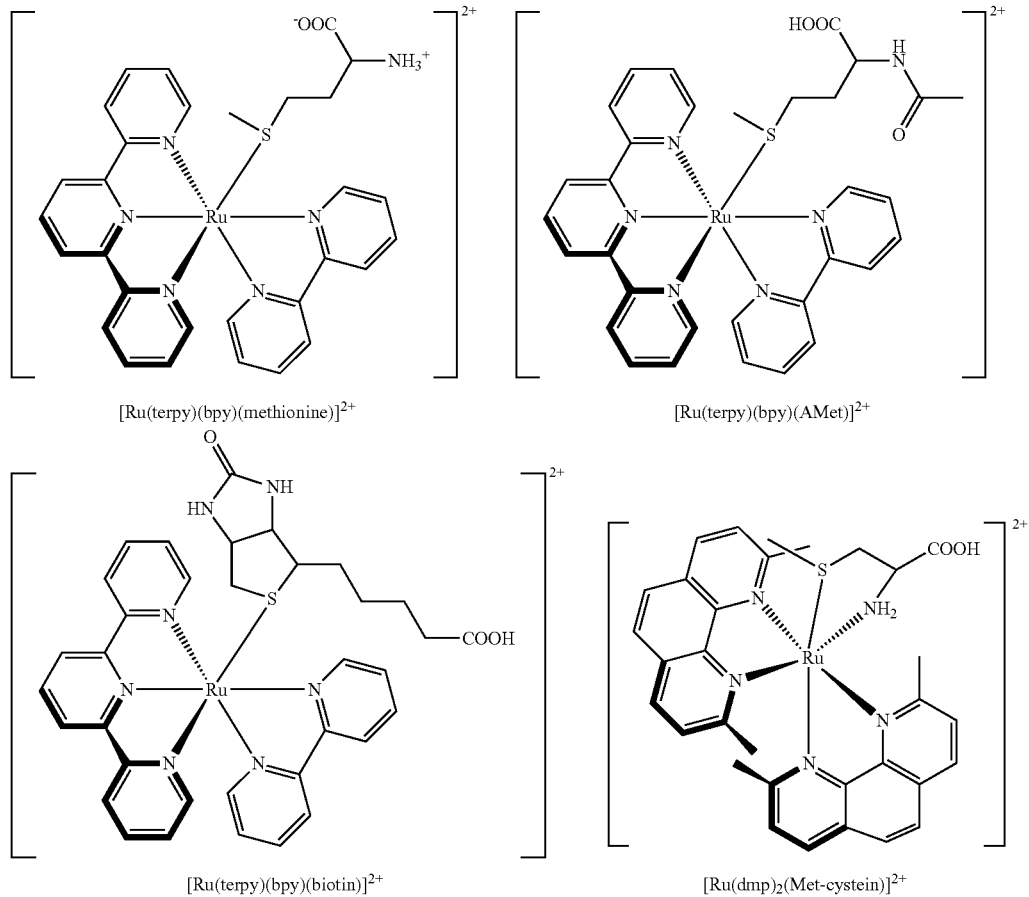

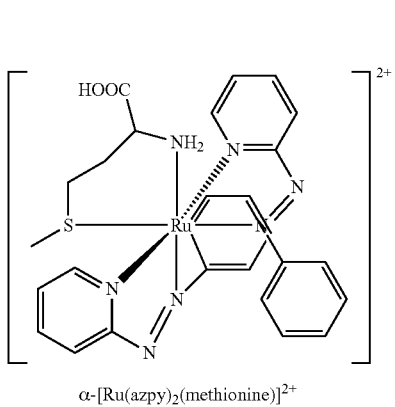
α-[Ru(azpy)₂(methionine)]²⁺
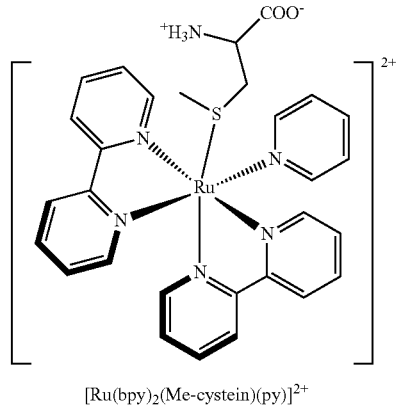
[Ru(bpy)₂(Me-cystein)(py)]²⁺
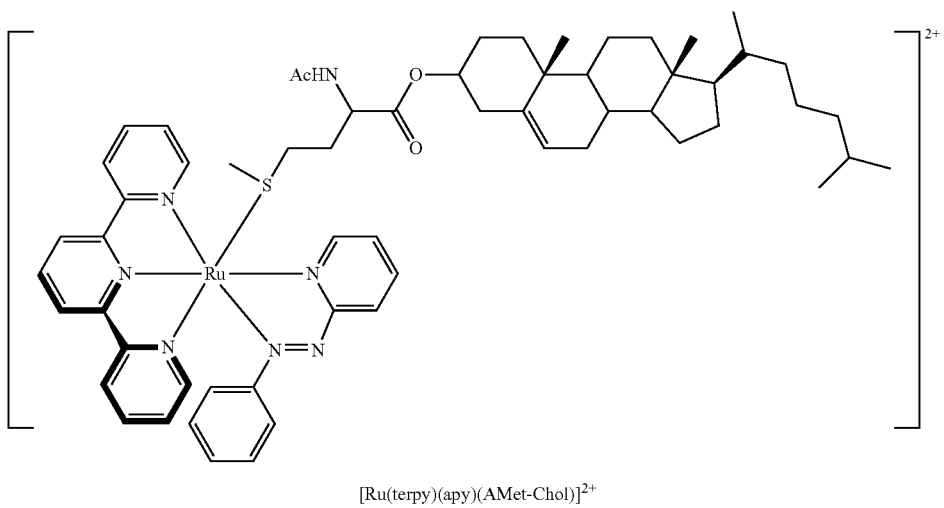
[Ru(terpy)(apy)(AMet-Chol)]²⁺
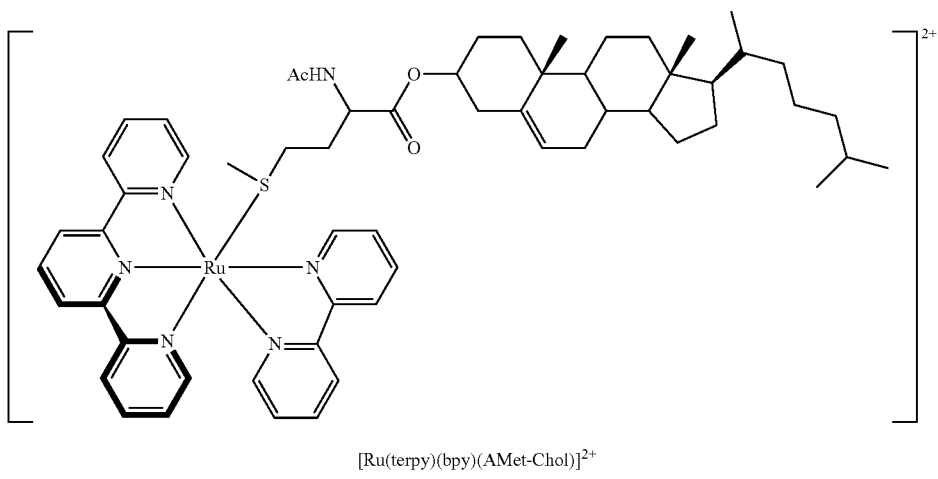
[Ru(terpy)(bpy)(AMet-Chol)]²⁺

-continued

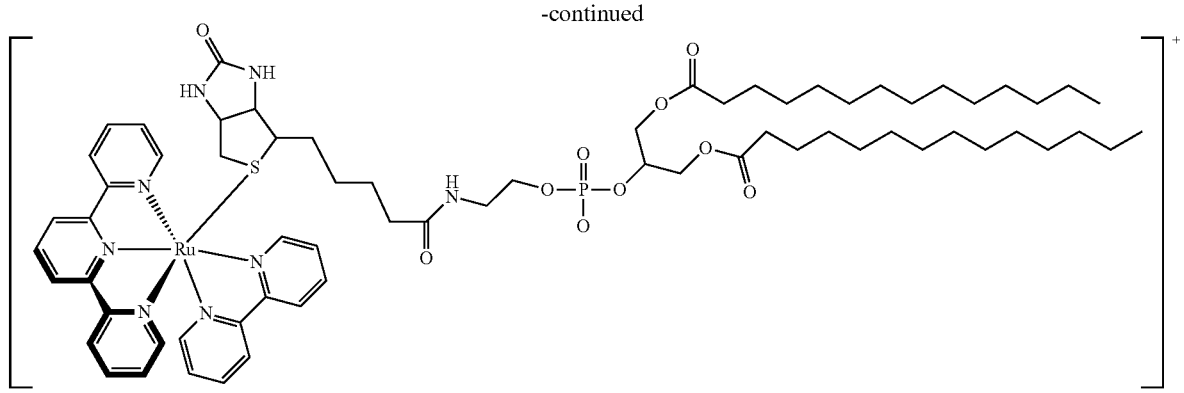

[Ru(terpy)(bpy)(biotin-DMPE)]$^{2+}$

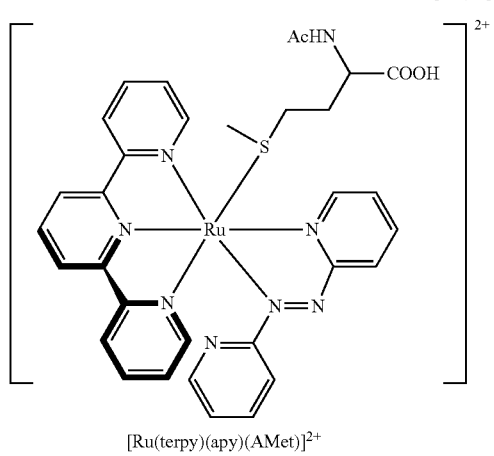

[Ru(terpy)(apy)(AMet)]$^{2+}$

In order to render the compounds of the present invention biologically active or more biologically active, the compounds of the present invention are subjected to light, so as to convert the compounds from substantially non-biologically active or poorly biologically active, to compounds that are highly biologically active. In terms of complexes which may display a degree of biological activity, it is desired that the light activation results in a greater than 2-fold, such as a greater than 5, or 10, or even a 100 fold improvement in biological activity, which may be determined in an appropriate manner, such as an $IC_{50}$, minimum inhibitory concentration, $EC_{50}$, half maximal effective concentration, or other biological activities which can be determined by a skilled addressee.

A feature of the present invention is that the light activation desirably takes place in the body, or within cells, and that the photocleavable group Y initially bound to ruthenium is photosubstituted for an aqua, hydroxo, or a biological ligand, as found in a biological environment, such as within a cell, or blood. The new ruthenium complex may have enhanced biological activity, such as cytotoxicity, in this light-activated form. Meanwhile, the photoreleased sulfur-containing group Y is also released in the same biological environment. Depending on the biological activity of the free sulfur-containing ligand Y, which might be high or low, the biological activity of the active form of the ruthenium complex, combined to the biological activity of the free sulfur-containing ligand Y, is expected to be different from the biological activity of the initial R—Y metal conjugate.

Light of any suitable wavelength may be used to cause activation of the complexes of the present invention. However, desirably the light may be in the visible ranges, i.e. with a wavelength between 400 and 800 nm. Alternatively, near infrared radiation might be used that penetrate better into biological tissues. Two-photon absorption may be realised using very intense near infrared light beams, where an equivalent excitation corresponding to a light of 400-450 nm is obtained by the simultaneous absorption by the ruthenium complex of two photons of 800-900 nm, respectively.[9]

Light penetration in biological tissues increases with wavelength, and long wavelengths are preferable for photothera-peutic applications. PDT studies have shown that the light penetration depth generally increases with wavelength due to the light absorption by biological chromophores such as haemoglobin or melanin. UV light certainly is not suitable to activate a prodrug in vivo, as 1) it does not penetrate into biological tissues, and 2) it destroys living cells. Visible or near infrared light, on the contrary, are not harmful, and penetrate further into biological tissues. Thus, an advantage of the compounds of the present invention is that they are able to be photoactivated/cleaved at wavelengths in the visible or near infra-red.

Suitable light sources include those which are capable of emitting light of the appropriate wavelengths, for example and without limitation, commercially available tungsten lamps (Cole-Parmer), arc lamps, xenon continuous lamps, lasers, e.g., blue lasers or photooptic light sources, and laser diodes. Such light sources are commercially available (CrystaLaser, Reno, Nev.; Lasever, Jiangdong, Ningbo, China, Lot-Oriel, Müller GmbH Elektronik-Optik). Other forms of light, such as sunlight, infrared light, pulsed infrared light, or UV radiation can also be used for the invention, as necessary or desired.

Devices and systems suitable for exposing the photosensitive compounds to light, particularly visible or infrared light, further include imaging probes, imaging catheters and fiber optic probes, particularly those containing gradient index, or graded-index, (GRIN) lenses, which are described in U. Utzinger et al., 2003, J. Biomed. Optics, 8 (1): 121-147; and Fujimoto et al., Photoyaic Materials, Devices and Systems-Laser Medicine and Medical Imaging Group, RLE Progress Report 144, pp 27-1 to 27-35, and which are commercially available. (Sp3 plus, UK). The light suitable for exposing the photosensitive compounds to photorelease the biologically active metal complex comprises a wavelength of about 350 to about 1000 nm. Preferred are visible or infrared light.

Further in accordance with this invention, the biologically active compound can also be released via one-photon or two-photon photolysis. Optical memories that utilize a two-photon excitation are described, for example, by Strickler and Webb.[10] A feature of two-photon excitation is the elimination of out-of-focus background.[11] Thus, two-photon processes can release a biologically active compound only in the plane of focus.[12]

The light for exposing the compounds according to the methods of this invention can be sunlight, photo-optic light, or laser light. Advantageously, in the methods of this invention, the light for exposing the compound is other than UV radiation. Thus, for example, the light can be visible light or infrared light, including one-photon and two-photon light. The light can be emitted from a variety of sources, including without limitation, a laser light source, a tungsten light source, a photooptic light source, etc.

Another advantage of visible light to expose or irradiate the compounds of the invention relates to the convenience and ability to use a visible light microscope, for example, to view a sample into which a compound is introduced and to microscopically visualize or monitor a photoreleased ruthenium complex from the compound after exposure to visible light. Because many microscopes do not transmit UV light, it is advantageous to be able to use a non-quartz microscope in accordance with this invention. Yet another advantage to the use of visible light is that it is not detrimental to living cells and tissues, making it beneficial for clinical use. In addition, for patient use, the light can be specifically directed to an area where a photosensitive ruthenium compound is introduced or administered by the use of laser technology, fibers, probes, tubes, and the like. Such probes, fibers, or tubes can be directly inserted, for example, into a body cavity or opening, or under or through the skin, to expose the biologically inactive, or poorly active, ruthenium complex to light and activate it.

In another of its embodiments, the present invention embraces a method of making an organic molecule bioavailable to a subject. The organic molecule can be made bioavailable to a localized body region or area of the subject, or systemically to the whole body. Local bioavailability of the photosensitive ruthenium compound is achieved, for example, via delivery devices and methods that allow the compounds to be directly administered, for example, inserted into a body cavity, or opening, through or into the skin, or into a tumor or lesion. The method of this embodiment involves administering a biologically unactive or poorly active metal compound to the subject, and exposing the compound to light under conditions sufficient to break the bond between the ruthenium and the sulfur atom, thereby making the biologically active compound bioavailable to the subject, and/or to a body site or region of the subject. The exposure to light can comprise the use of probes, fibers, tubes, and the like, which allow the light to be specifically directed to the area of interest on or within the body. Alternatively, the biologically unactive or poorly active compound can be administered to the patient kept in the dark; for photoactivation of the ruthenium compound, the patient can be moved to the light where exposure to light and photorelease of the biologically active ruthenium compound and sulfur-based ligand occurs.

The complexes of the present invention are typically positively charged. Thus, a counter-ion is necessary to balance the charge of the complex and provide a molecular species with an overall charge of zero.

Negatively charged counter ions may be any suitable ion, for example selected from $BF_4$, $BPh_4$, $PF_6$, triflate, mesylate, tosylate, trisphat, halides (such as chlorides), nitrate, sulfate, carbonate and phosphate.

The counter ion may be chosen for certain purposes, for example, large non-binding anions may be preferred, such as $BPh_4$, tosylate, $PF_6$, or $BF_4$, which tends to provide a water-insoluble complex thereby providing a useful advantage during a recovery stage of the compound preparation, e.g. for separation out of an aqueous solution. In addition, a water-insoluble compound may have good solubility in an organic solvent, which might be used during purification as well. On the contrary, polar, binding counter-anions such as halides, nitrate, sulfate or carbonate may provide good water solubility to the metal complex, which can be used to tune the final formulation of the drug.

The counter ions may be chosen to provide a useful solubility for preparation of the complexes and the same counter ion may be retained or exchanged for another counter ion to provide a compound better suited for pharmaceutical/medical uses.

For example, triflate may be selected, or chloride, bromide or iodide to provide more water-soluble compounds.

Viewed from a second aspect, the invention provides a compound of the first aspect, or an embodiment thereof, or pharmaceutically acceptable salt, solvate, ester, or amide thereof, for use in medicine.

Viewed from a third aspect, the invention provides a composition comprising a compound of the first or second aspect, or an embodiment thereof or pharmaceutically acceptable salt, solvate, ester, or amide thereof, together with a pharmaceutically acceptable carrier.

Viewed from a further aspect, the invention provides a method of treatment or prophylaxis of a disease involving cell proliferation, in particular cancer, said method comprising administering a therapeutically or prophylactically useful amount of a composition of the invention, or pharmaceutically acceptable salt, solvate, ester, or amide thereof, to a subject in need thereof and irradiating the compound with visible of near infra-red light.

Viewed from a further aspect, the invention provides use of a compound of the invention, or pharmaceutically acceptable salt, solvate, ester, or amide thereof, in the manufacture of a medicament for use in any method of treatment or prophylaxis as defined herein.

In accordance with the present invention the term "biological activity" is understood to relate to any suitable biological activity, such as cytotoxic, anti-microbial, anti-viral, anti-inflammatory, anti-diabetic, cardiovascular, anti-psychotic, analgesic, anti-rheumatics, anti-autoimmune, anti-neurodegenerative, anti-toxin, steroidal, hormonal, wound-healing. Essentially the present invention may find application in a situation where it may be desirable to initially administer a biological agent in a substantially inactive or poorly active form and subsequently activate the agent, suitable reasons may include undesirable general toxicity, cost of the drug, biological half-life and the like. In such situations it may be desirable to be able to only activate a biologically active agent at its desired site of action.

In one embodiment, the invention relates to the provision of cytotoxic agents, which may be of use in treating conditions associated with abnormal proliferation of cells. Examples of such diseases include cancers, hyperproliferative disorders (including warts, psoriasis, inflammatory bowel disease), rheumatoid/autoimmune conditions, sickle cell anemia and thalasemias.

Examples of cancers which may be treated include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumor of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronic myelogenous leukaemia's, myelodysplastic syndrome, or promyelocytic leukaemia; thyroid follicular cancer; a tumor of mesenchymal origin, for example fibrosarcoma or habdomyosarcoma; a tumor of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

The compounds of the present invention may find particular application in treating cancer as their administration may be minimally invasive, spatially accurate, and as they can reach places where surgery is impossible. Due to the light activation of the compounds of the present invention, they may be particularly suited for skin, lung, or digestive track cancers, for which a source of light can easily be directed onto the tumor. However, it is also possible to shine light on internal organs using endoscopy, to cure, for example prostate, head and neck, bile duct, or bladder cancers for example. They may also be administered following or during a surgical procedure to remove a tumor, where the compound may be administered to the region of tumor resection and light applied accordingly.

Other therapeutic agents (e.g. antineoplastic agents) may be administered together (whether concurrently or at different time intervals) with the compounds/compositions of the invention. Examples of such other therapeutic agents include but are not limited to topoisomerase inhibitors, alkylating agents, antimetabolites, DNA binders and microtubule inhibitors (tubulin target agents), such as cisplatin, cyclophosphamide, doxorubicin, etoposide, irinotecan, fludarabine, 5FU, taxanes or mitomycin C. Other therapeutic agents will be evident to those skilled in the art. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where a compound of the invention is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery, and controlled diets.

The patient is typically an animal, e.g. a mammal, especially a human.

By a therapeutically or prophylactically effective amount is meant one capable of achieving the desired response, and will be adjudged, typically, by a medical practitioner. The amount required will depend upon one or more of at least the active compound(s) concerned, the patient, the condition it is desired to treat or prevent and the formulation of order of from 1 μg to 1 g of compound per kg of body weight of the patient being treated.

Different dosing regiments may likewise be administered, again typically at the discretion of the medical practitioner. As alluded to hereinafter the low toxicity of the compounds of the invention, allow for at least daily administration although regimes where the compound(s) is (or are) administered more infrequently, e.g. every other day, weekly or fortnightly, for example, are also embraced by the present invention.

By treatment is meant herein at least an amelioration of a condition suffered by a patient; the treatment need not be curative (i.e. resulting in obviation of the condition) but may be palliative. Analogously references herein to prevention or prophylaxis herein do not indicate or require complete prevention of a condition; its manifestation may instead be reduced or delayed via prophylaxis or prevention according to the present invention.

For use according to the present invention, the compounds or pharmaceutically acceptable salt, solvate, ester, or amide thereof described herein may be presented as a pharmaceutical formulation, comprising the compound, or pharmaceutically acceptable salt, solvate, ester, or amide thereof, together with one or more pharmaceutically acceptable carriers therefor and optionally other therapeutic and/or prophylactic ingredients. Any carrier(s) are acceptable in the sense of being compatible with the other ingredients of the formulation and not deleterious to the recipient thereof.

Examples of pharmaceutically acceptable salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Pharmaceutically acceptable salt, solvate, ester, or amide thereof may be physiologically functional derivatives of the compounds of the present invention. Such physiologically functional derivatives may also be referred to as "pro-drugs" or "bioprecursors". Physiologically functional derivatives of compounds of the present invention include in vivo hydrolysable esters or amides, particularly esters. Determination of suitable pharmaceutically acceptable esters and amides is well within the ability of those skilled in the art.

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of formulae (I) or (II) as well as wholly or partially racemic mixtures of such enantiomers.

The compounds of the present invention may be prepared using reagents and techniques readily available in the art and/or exemplary methods as described hereinafter.

Pharmaceutical formulations include those suitable for oral, topical (including dermal, buccal and sublingual), rectal or parenteral (including subcutaneous, intradermal, intramuscular, intraperitoneal, and intravenous, subcutaneous, epidural, topical, transdermal, parenteral, intrathecal, vaginal, rectal, colorectal, oral, intracranial, retroorbital, intrasternal), nasal and pulmonary administration e.g., by inhalation. The formulation may, where appropriate, be conveniently presented in discrete dosage units and may be prepared by any of the methods well known in the art of pharmacy. Methods typically include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams, or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

The contents of each literature and patent reference referred to herein is hereby incorporated by reference in its entirety as if the entire contents of each of these references were recited herein in full.

BRIEF DESCRIPTION OF THE DRAWINGS

The present invention will now be further described with reference to the following examples and figures which shows.

DETAILED DESCRIPTION

Figure 1:
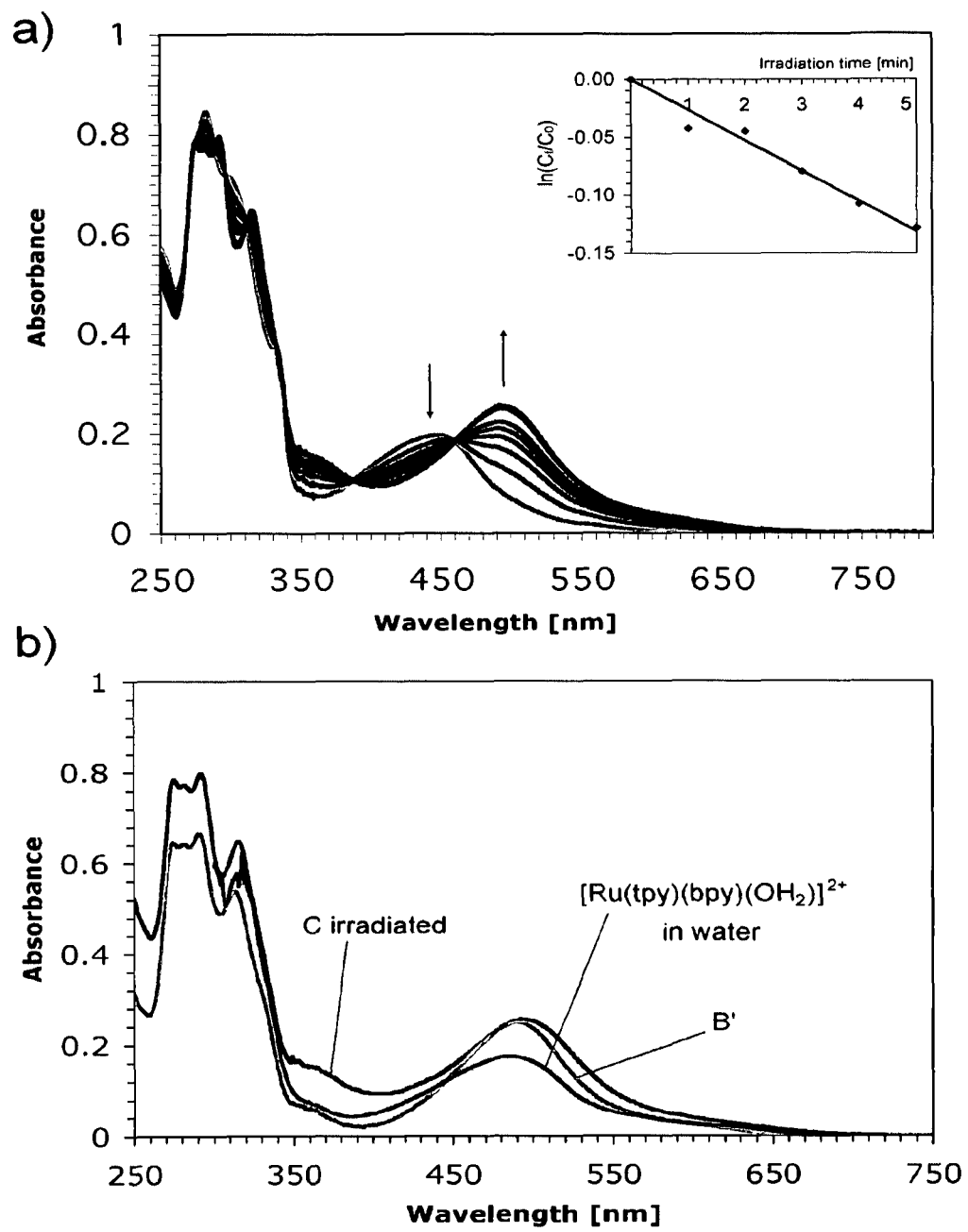
FIG. 1. a) Evolution of the UV-visible spectrum of sample C upon white light irradiation at 25° C. in a pH=7.0, chloride-free phosphate buffer (t=0, 1, 2, 3, 4, 5, 10, and 15 min). Insert shows the evolution of $\ln(C_t/C_0)$ as a function of irradiation time t, where $C_t$ and $C_0$ stand for the concentration in $[5]^{2+}$ at time t and t=0, respectively. b) Superimposed UV-visible spectra of sample C after irradiation (black), sample B' (orange), and a reference sample of $[Ru(terpy)(bpy)(OH_2)](BF_4)_2$ in water (red).

List of Abbreviations apy 2,2'-azobis(pyridine)
azpy 2-phenylazopyridine
bpy 2,2'-bipyridine
AMet N-acetyl-L-methionine
DNA deoxyribonucleic acid
terpy 2,2':6',2''-terpyridine Example 1

Herein, we consider ligand photosubstitution reactions of $[Ru(terpy)(bpy)(Y)]^{2+}$ complexes at the water-bilayer interface of a liposome. By covalent linkage of a monodentate ligand Y (here a thioether) to a membrane intercalator like 3β,5α-cholestanol, and coordination of the sulfur ligand to ruthenium, liposomes are decorated with ruthenium complexes, which can be cleaved from the bilayer by visible light irradiation.

Experimental Section
General.

Acetone was dried on potassium carbonate and distilled prior to use. $KNO_3$ was used as a saturated aqueous solution, aqueous $KPF_6$ was 40 g·L$^{-1}$. $^1H$ (300.1/400.0 MHz) and $^{13}C$ (75.5/100.6 MHz) NMR spectra were recorded on a Varian INOVA 300 MHz or 400 MHz spectrometer; $^{31}P\{^1H\}$ (121.5 MHz) and $^{19}F$ (376 MHz) NMR spectra were recorded on a Varian INOVA 400 MHz spectrometer. Chemical shift values are reported in ppm (δ) relative to $Me_4Si$ ($^1H$ and $^{13}C$ NMR). MS measurements were carried out on an Applied Biosystems Voyager DE-STR MALDI-TOF MS. Elemental analyses were performed by H. Kolbe Microanalysis Laboratories, Wilheim, Germany. UV-vis absorption spectra were taken on a Cary 5 spectrophotometer from Varian. For column chromatography, Merck silica gel 60 (230-400 mesh) was used.

All standards reagents were purchased from Acros Organics and Aldrich Chemical Co. Inc, and used as received. [Ru(terpy)(bpy)(OH$_2$)][BF$_4$)$_2$[13] and [Ru(terpy)(bpy)(Cl)](Cl)[13] were obtained as described in the literature. Cholesterol, bromoacetylchloride, sodium thiomethoxide, acetic acid were from commercial sources and used as received. 1,2-dimyristoyl-sn-glycero-3-phosphoglycerol (DMPG) and 1,2-dimyristoyl-sn-glycero-3-phosphocholine (DMPC) were obtained from Avanti Polar Lipids and stored at −18° C. A chloride-free buffer solution was prepared by mixing KH$_2$PO$_4$ (313 mg, 2.3 mmol), K$_2$HPO$_4$.3H$_2$O (593 mg, 2.6 mmol), K$_2$SO$_4$ (849 mg, 4.87 mmol) in a 500 mL volumetric flask and dissolving with MilliQ water (pH=7.03 at 23° C.). All photosensitive solutions were protected from light by aluminum foil.

Synthesis.

Compound 2 was obtained by hydrogenation of cholesterol. To a solution of 1 (7.73 g, 20 mmol) in tetrahydrofuran (20 mL) were added palladium on charcoal (400 mg, 10%) and acetic acid (1.7 mL). This mixture was transferred in a Parr apparatus and subjected to hydrogenation at 60° C. under 5 bars of H$_2$ until consumption of H$_2$ ceased (~45 min). The cooled mixture was filtered on celite, the celite washed twice with THF (30 mL), the gathered organic phase evaporated to dryness, and the crude product recrystallized from hot hexane (30 mL) down to 4° C. to give 5α-cholestan-3β-ol (compound 2, 5.90 g, 76%).

Compound 3:

To a solution of 2 (5.90 g, 15.2 mmol) in dry tetrahydrofuran (100 mL) was added bromoacetylchloride (4.5 mL, 53.1 mmol). The solution was heated to reflux for 2 h, the solvent evaporated on a rotary evaporator, and the minimum amount of hot hexane was added to dissolve the crude product. After cooling down to room temperature the hexane solution was left in the fridge overnight to yield after filtration and drying bromoacetyl 5α-cholestan-3β-oate as a pale green crystalline solid (compound 3, 5.48 g, 71%). $^1$H NMR (400 Mhz, δ in CDCl$_3$): 4.75 (m, 1H, CHOCO), 3.79 (s, 2H, CH$_2$Br), 1.97 (dt, 1H, J 3.3, 12.4), 1.90-0.90 (m, 29H), 0.89 (d, 3H, J 6.5), 0.87 (d, 3H, J 6.6), 0.85 (d, 3H, J 6.6), 0.82 (s, 3H), 0.65 (s+m, 4H). $^{13}$C NMR (101 MHz, δ in CDCl$_3$): 166.92, 77.48, 77.16, 76.84, 76.13, 56.54, 56.41, 54.32, 44.76, 42.73, 40.11, 39.66, 36.80, 36.31, 35.94, 35.60, 35.58, 33.83, 32.10, 28.72, 28.38, 28.15, 27.35, 26.58, 24.34, 23.98, 22.96, 22.71, 21.36, 18.82, 12.37, 12.21. ESI MS exp (calc): 531.26 (531.28, [M+Na]$^+$), 1041.4 (1041.6, [2M+Na]$^+$), 1551.4 (1551.9, [3M+Na]$^+$). C,H,N exp: 68.45/9.75/0.00; calc: 68.35/9.69/0.0 for C$_{29}$H$_{49}$BrO$_2$.

Compound 4:

Compound 3 (1.02 g, 2.0 mmol) and sodium thiomethoxide (289 mg, 4.12 mmol) were weighed in a round-bottom flask and put under N$_2$. Dry tetrahydrofuran (50 mL) was cannulated under N$_2$ and the suspension was heated to reflux for 2 h. THF was removed under vacuum, 100 mL of water were added and the product extracted with Et$_2$O (3×75 mL). The combined ether fractions were washed with water, brine, dried with MgSO$_4$, filtered and evaporated to dryness. Column chromatography on silica gel (200 mL) using pentane:dichloromethane mixtures (8:3 to 1:1) afforded ligand 4 as a white solid (785 mg, 82%). $^1$H NMR (400 Mhz, δ in CDCl$_3$): 4.74 (m, 1H, 3α), 3.14 (s, 2H, SCH$_2$O), 2.20 (s, 3H, CH$_3$S), 2.0-0.93 (m, 25H), 0.89 (d, 3H), 0.85 (dd, 6H), 0.82 (s+m, 4H). $^{13}$C NMR (100.6 Mhz, δ in CDCl$_3$): 169.95 (COO), 74.93 (CH$^\alpha$O), 56.54, 56.41, 54.34, 44.80, 42.72, 40.11, 39.65, 36.86, 36.30, 36.15, 35.93, 35.60, 34.09, 32.12, 28.74, 28.38, 28.14, 27.58, 24.34, 23.98, 22.96, 22.70, 21.35, 18.81, 16.37, 12.38, 12.21. ESI MS exp (calc): 499.355 (499.359, [M+Na]$^+$), 975.67 (975.72, [2M+Na]$^+$), 1451.8 (1452.1, [3M+Na]$^+$). C,H,N exp: 75.69/11.00/0.00; calc 75.57/10.99/0.0 or C$_{30}$H$_{52}$O$_2$S.

Compound [5](PF$_6$)$_2$:

[Ru(terpy)(bpy)(Cl)](Cl) (150 mg, 0.27 mmol) and ligand 4 (138 mg, 0.29 mmol) were weighed in a round-bottom flask and put under N$_2$. Dry, degassed acetone was added (20 mL), and an acetone solution of AgBF$_4$ (113 mg, 0.58 mmol) was cannulated under N$_2$. The reaction mixture was heated at reflux overnight (16 h), cooled to room temperature, filtered over celite, and acetone removed under vacuum. The crude product was purified by chromatography on silica gel (200 mL) using an acetone/water/KNO$_{3sat}$ mixture (100:10:1). The bright orange fraction was collected, 50 mL of aqueous KPF$_6$ were added, acetone was removed on a rotary evaporator, and the precipitate filtered on glass filter, washed thoroughly with water, Et$_2$O, and dried under vacuum. Yield: 94 mg of compound 4 as a bright orange solid (50%). $^1$H NMR (400 Mhz, δ in acetone-d$_6$): 10.1 (dd, 1H, A2), 8.94 (d, 3H), 8.74 (d, 2H), 8.71 (d, 1H), 8.52 (m, 2H), 8.20 (m, 3H), 8.01 (m, 3H), 7.53 (m, 3H), 7.31 (m, 1H), 4.45 (m, 1H, CH$^\alpha$O), 3.00 (s, 2H, SCH$_2$O), 1.62 (s, 3H, CH$_3$S), 2.02-0.82 (m, 39H), 0.78 (s, 3H), 0.67 (s+m, 4H). $^{13}$C NMR (100.6 Mhz, δ in acetone-d$_6$): 166.9, 159.1, 158.4, 157.74, 157.66, 154.7, 153.3, 150.9, 140.0, 139.3, 138.2, 129.5, 128.7, 128.3, 126.1, 125.7, 125.4, 124.9 (18 C$_{arom}$), 76.5 (CH$_2$O), 57.28, 57.15, 55.01, 45.24, 43.35, 40.84, 40.23, 37.24, 36.92, 36.89, 36.58, 36.25, 36.08, 34.52, 32.69, 29.22, 28.89, 28.67, 27.95, 24.83, 24.51, 23.06, 22.82, 21.89, 19.07, 15.58, 12.46, 12.41 (SMe+ 27 C$_{alkyl}$). $^{19}$F NMR (376.3 Mhz, δ in acetone-d$_6$): −72.9 (d, J$_{F-P}$=707.8 Hz). UV-vis: λ$_{max}$ in nm (ε in cm·M$^{-1}$): 454 (7760), 328 (15900), 332 (15900). ESI MS exp (calc): 483.709 (483.719 for C$_{57}$H$_{75}$N$_5$O$_3$RuS, [M-2PF$_6$]$^{2+}$). C,H,N exp: 52.59/5.69/5.32; calc: 52.54/5.69/5.57 for C$_{55}$H$_{71}$F$_{12}$N$_5$O$_2$P$_2$RuS.

Vesicle Preparation.

Aliquots of phospholipids (0.00☐ mmol) and ligand 4 or complex [5](PF$_6$)$_2$ (1-25 mol %, see Table 1) were mixed from chloroform stock solutions and dried under a flow of nitrogen for a few hours. They were subsequently placed under vacuum to remove traces of chloroform. Then the lipid mixtures were hydrated in a chloride-free buffer containing 10 mM of phosphates and 40 mM of K$_2$SO$_4$ (total ionic strength 50 mM), at pH=7.0. The final concentration of the lipids was 2.5 mM. The lipid suspensions were freeze-thawed ten times (from liquid N$_2$ temperature to +50° C.), and then extruded ten times (at +50° C.) through 200 nm polycarbonate filters. The vesicle-containing samples were conserved in the dark at 4° C. and used within 5 days.

Dynamic Light Scattering:

Vesicle size was determined by dynamic light scattering in a Zetasizer (Malvern Instruments Ltd., U.K.), operated at a wavelength of 633 nm.

Irradiation and Quantum Yield Measurement.

White light irradiations were performed using the 150 W halogen lamp of a microscope; the sample to irradiate was placed in a water bath at 25° C. to filter IR and UV radiations, and the reaction was followed by UV-vis spectroscopy. For quantum yields determination the continuous beam of a 1000 W Xenon arc lamp from Lot was filtered by a water filter of 15 cm diameter followed by an Andover 452FS10-50 interference filter from Lot Oriel ($\lambda_{ex}$=452 nm). 3 mL samples containing the vesicles (1.25 mM) functionalized with 5 mol % of [5](PF$_6$)$_2$ were put in a closed, UV-vis quartz cell (path length: 1 cm) under an air atmosphere, and stirred in a water bath at 25° C. Under these conditions, a light intensity of 6.4(3)·10$^{-8}$ einstein·s$^{-1}$ was measured using standard ferrioxalate actinometry (see Supporting Information).[14] The extinction coefficients of [Ru(terpy)(bpy)(OH$_2$)]$^{2+}$ at the excitation wavelength (452 nm), and in presence of the ligand-functionalized vesicles, were determined by adding known amounts of the complex to vesicle solutions containing 5 mol % of ligand 4 (values found: $\epsilon_{452}$=10800 cm·M$^{-1}$ for DMPG and 9750 cm·M$^{-1}$ for DMPC). From the evolution of the UV-vis spectra of the vesicle-containing solution, the variation of $C_t$, the concentration in complex [5]$^{2+}$, was determined as a function of irradiation time t, and a linear regression of ln($C_t/C_0$) as a function of t gave a pseudo first-order rate constant of 2.34·10$^{-3}$ s$^{-1}$ for DPMG, and 2.27·10$^{-3}$ s$^{-1}$ for DPMC. The quantum yield for the photosubstitution of ligand 4 by H$_2$O at vesicles was calculated to be 0.0074(8) for DMPG and 0.0073(8) for DMPC.

Ultracentrifugation.

The UV-visible spectrum of a freshly prepared vesicle sample was first measured between 250 and 800 nm. 1.0 mL of the sample was ultracentrifuged at 25° C. and 100 krpm (RCF 35 500 g) for one hour. 0.70 mL of the supernatant was pipetted out, and its UV-visible, spectrum was measured. The lipid content of the supernatant was measured by a Rouser assay[15] after Bligh and Dyer extraction.[16] The Bligh and Dyer method was used to extract the phospholipids from the aqueous phase as follows: to each sample (0.4 mL) was added methanol (1.2 mL) and chloroform (0.5 mL), and the mixture was homogenized. It was then extracted 3 times by adding chloroform (0.5 mL), mixing, centrifugation at 3000 rpm (RCF 1620 g) for 3 min, and removal of the chloroform phase. The combined organic fractions were evaporated under a flow of N$_2$ for one hour, and dried under vacuum for 30 min. The Rouser assay consists of a spectrophotometric titration of the phosphate concentration using a molybdate salt: each extracted sample was decomposed with HClO$_4$ (0.3 mL, 70-72%) at 180° C. for 1 h. After cooling of the samples to room temperature water (1 mL) was added, followed by ammonium heptamolybdate (0.4 mL, 1.25% w/v) and ascorbic acid (0.4 mL, 5% w/v), and the samples were cooked 5 min in boiling water, using marbles as stoppers to prevent evaporation. The absorbance of the solution at 797 nm was measured and compared to a calibration curve obtained using 6 samples containing 0, 10, 20, 30, 40, 50 nmol of phosphate and prepared in exactly the same conditions. Typical linear regression coefficients $R^2$=0.9997 were found, and the amount of lipids found in the supernatant after ultracentrifugation was calculated accordingly.

Results

Ligand Synthesis and Coordination to Ruthenium.

The three-step synthesis of ligand 4 is shown in Scheme 6: hydrogenation of cholesterol was achieved first, followed by esterification with bromoacetylchloride, and nucleophilic substitution of the bromide by a methanethiolate group. Coordination of 4 to ruthenium was realized by reacting it with [Ru(terpy)(bpy)(Cl)](Cl) in presence of 2 equivalents of AgBF$_4$ in acetone, followed by column chromatography (see Scheme 7). Anion exchange using KPF$_6$ in excess yielded the water-insoluble orange complex [5](PF$_6$)$_2$, which was characterized by $^1$H, $^{19}$F and $^{13}$C NMR, mass spectrometry (ESI-MS), elemental analysis, and UV-visible spectroscopy. Coordination of the sulfur atom of 4 to the ruthenium atom in complex [5](PF$_6$)$_2$ is characterized by an absorption maximum at 454 nm in acetone,[17] as well as by a low-field shifted doublet for the A2 proton on the bipyridine in $^1$H NMR spectroscopy ($\delta$=10.1 ppm in acetone-d$_6$, see Scheme 7 for notations).[18]

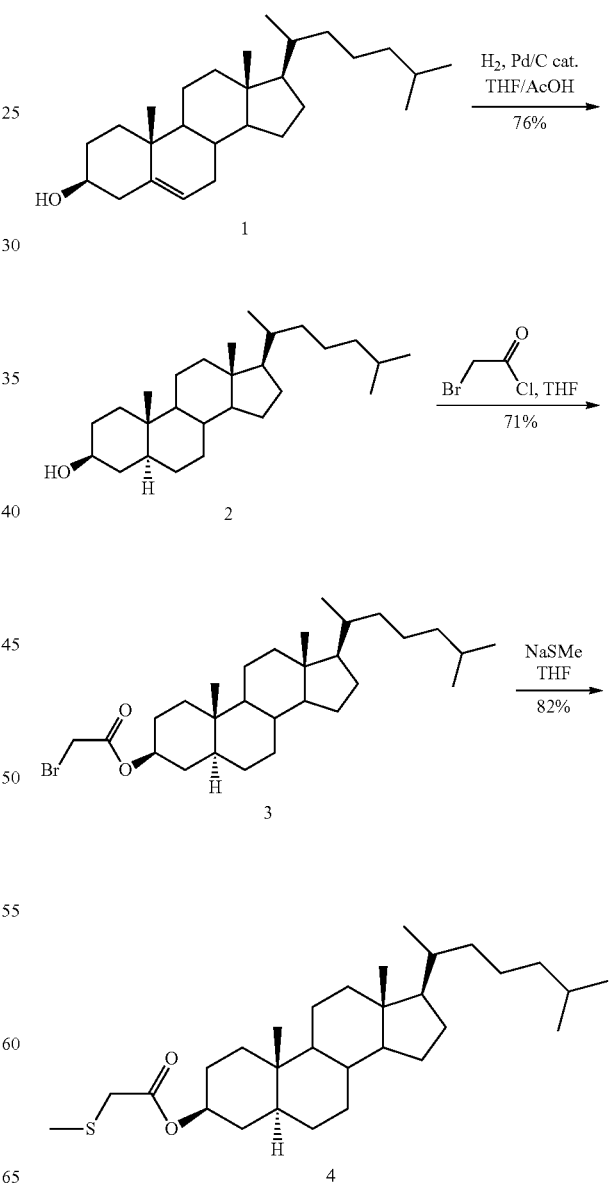

Scheme 6. Synthesis of ligand 4.

Scheme 7. Synthesis of complex [5](PF$_6$)$_2$ and notation of the protons.

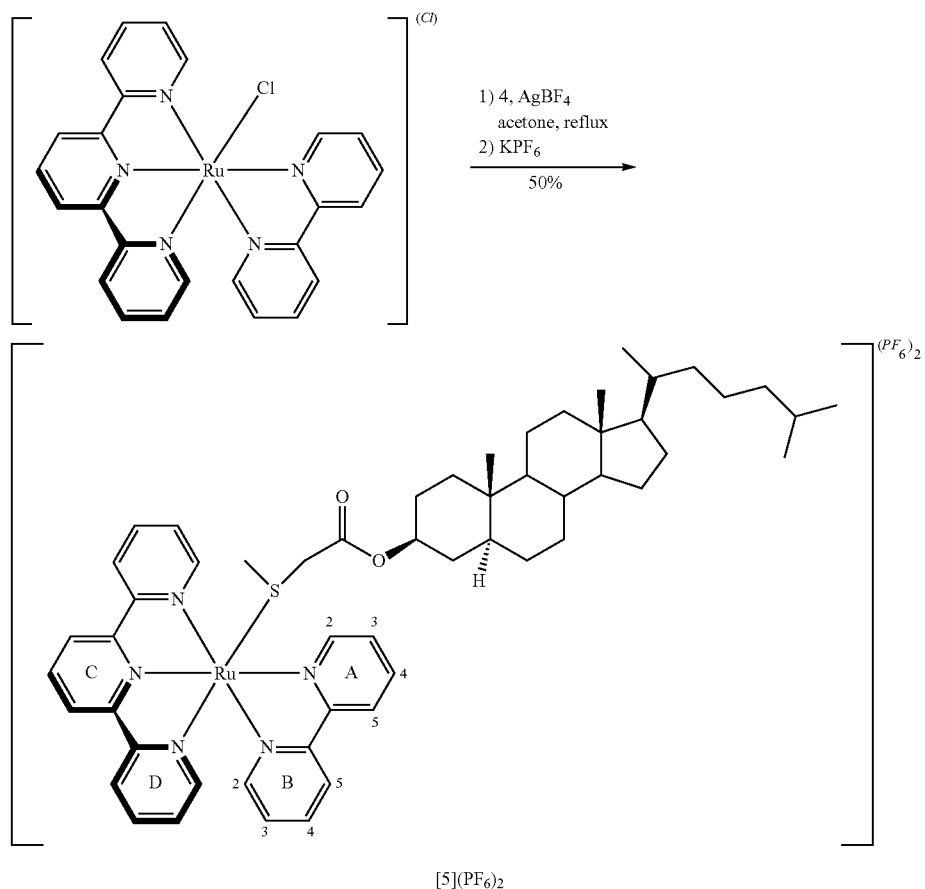

[5](PF$_6$)$_2$

Vesicle Preparation and Characterization.

Large unilamellar vesicles (LUVs) including 1 mol % of either complex [5](PF$_6$)$_2$ or ligand 4, were prepared as described in the Experimental Part. Eight types of samples were prepared as indicated in Table 1. Although [5](PF$_6$)$_2$ is not water-soluble, upon incorporation into the vesicles transparent yellow suspensions were obtained for sample C and F (i.e., those containing 1 mol % of [5](PF$_6$)$_2$). The UV-visible spectrum of the vesicle solutions showed the characteristic weak $^3$MLCT absorption bands of [5]$^{2+}$ in the visible region (absorption maximum at 450 nm), and several more intense bands in the UV region.

TABLE 1

Composition of samples A to F and characterization by Dynamic Light Scattering

| Sample | Lipid[a] | Additive[b,c] | $Z_{average}$ (nm) | Polydispersity Index |
|---|---|---|---|---|
| A | DMPG | — | 140.9 ± 6.1 | 0.038 ± 0.043 |
| B | DMPG | 4 | 156.3 ± 4.6 | 0.113 ± 0.059 |
| B' | DMPG | 4 + [Ru—OH$_2$]$^{2+}$ | 156.3 ± 4.6 | 0.113 ± 0.059 |
| C | DMPG | [5]$^{2+}$ | 160.1 ± 3.7 | 0.156 ± 0.030 |
| C irradiated | DMPG | [5]$^{2+}$ + hv | 167.8 ± 3.8 | 0.114 ± 0.034 |
| D | DMPC | — | 169.9 ± 7.2 | 0.070 ± 0.034 |
| E | DMPC | 4 | 177.8 ± 1.8 | 0.097 ± 0.032 |
| E' | DMPC | 4 + [Ru—OH$_2$]$^{2+}$ | 177.8 ± 1.8 | 0.097 ± 0.032 |
| F | DMPC | [5]$^{2+}$ | 155.1 ± 2.0 | 0.093 ± 0.033 |
| F irradiated | DMPC | [5]$^{2+}$ + hv | 155.7 ± 3.4 | 0.109 ± 0.024 |

[a]Lipid concentration is of 2.5 mM
[b]Unless otherwise noted, additives are introduced with a concentration of 1 mol % compared to the lipids
[c][Ru—OH$_2$]$^{2+}$ stands for [Ru(terpy)(bpy)(OH$_2$)](BF$_4$)$_2$ and is added after preparation of the vesicles.

Figure 2:
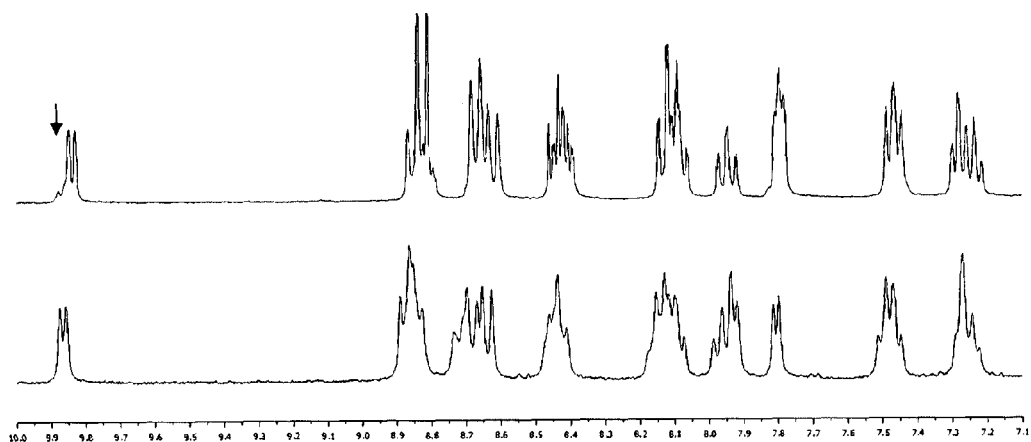
FIG. 2 shows an $^1H$ NMR spectrum of the aromatic part of compounds $[6](Cl)_2$ (top) and $[7](Cl)_2$ (bottom) in CD3OD. The arrow shows the A2 doublet (see Scheme 7) of the minor isomer for compound $[6](Cl)_2$.
Figure 3:
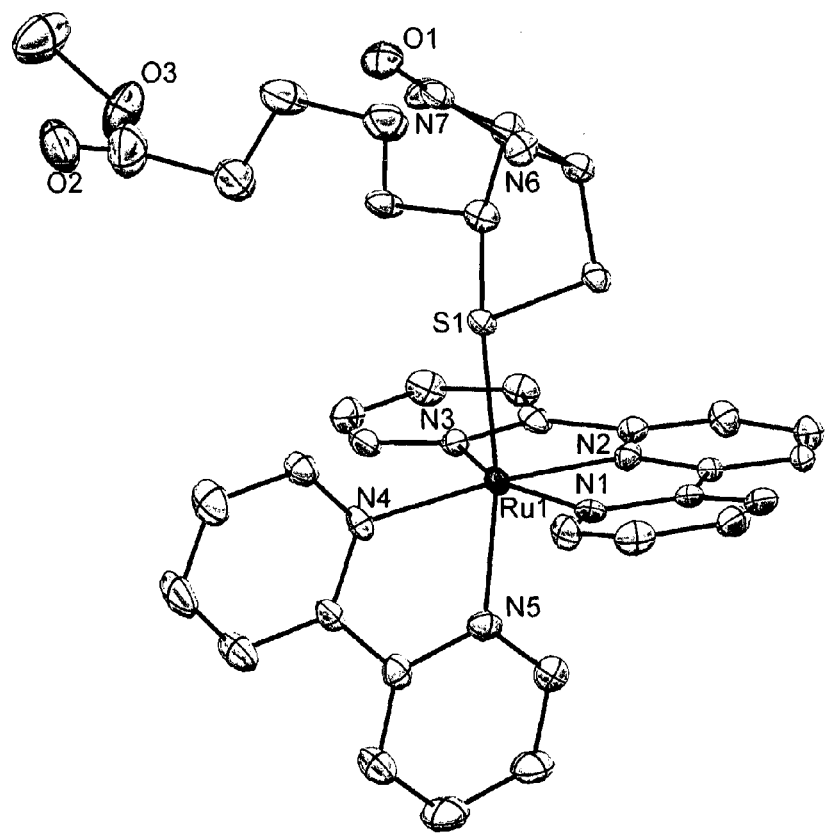
FIG. 3 shows the displacement ellipsoid plot (50% probability level) for the methyl ester [7Me]2+ dication observed in the crystal structure of [7Me]Cl2.(H2O) 4.MeOCH2CH2OH, obtained by vapour diffusion of toluene into a solution of $[7](Cl)_2$ in 2-methoxyethan-1-ol and MeOH. Counter-anions, H atoms, lattice solvent molecules, and disorder have been omitted for clarity
Figure 4:
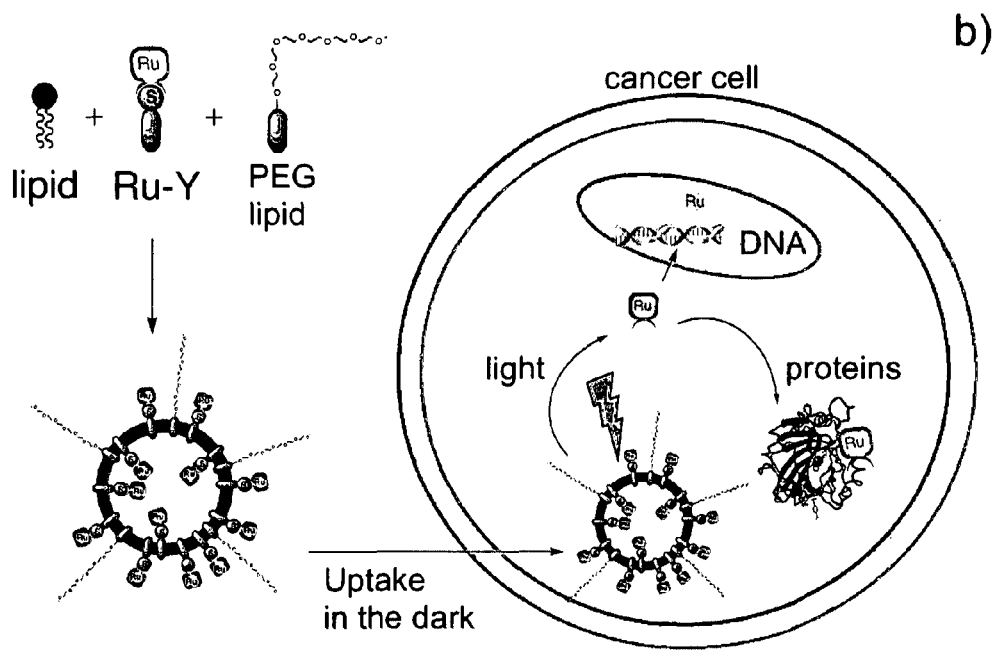
FIG. 4 shows the use of lipids and lipid-functionalized ruthenium complexes R—Y to attach the ruthenium complex via a photosensitive Ru—S bond to a liposome drug delivery system. The liposome is taken up by cancer cells, irradiation of the cancer cell releases the active aqua species, which interacts with DNA and/or proteins to kill the cell.

The size distribution of the vesicles was measured by dynamic light scattering (see Table 1). A narrow distribution centered between 140 nm and 180 nm was obtained, which is consistent with the nominal size of the filter holes used in the preparation (Ø 200 nm). In order to obtain more insight into the morphology of the vesicles, cryo-transmission electron microscopy (cryo-TEM) was performed by vitrification above T$_m$ on samples A-F (see FIG. 2).

With anionic lipids (DMPG, samples A-C) a relatively low concentration of vesicles was observed on the negatively charged support, probably due to repulsive electrostatic interactions. Samples of type A and B contained only unilamellar vesicles with a size compatible with DLS measurements (~150 nm). Sample C also contained unilamellar vesicles, but another type of structure was observed as well, which appeared as dark lines, ovoids or discs with a uniform contrast (see black arrow in FIG. 2c). Finally some of these unilamellar vesicles appeared facetted or as open bilayer fragments. On average, the diameter of the particles is roughly ~150 nm, which is consistent with DLS measurements. The bilayer thickness was 7±1 nm, which corresponds to the expected value for a single bilayer. Pixel size of the images was in the range of 1 nm, which limited the accuracy of the measurements.

When neutral DMPC lipids were used (samples D to F) a much higher number of vesicles was observed (see FIG. 2d-f), as there was no repulsive interaction with the negatively charged carbon support. Although the vesicles were mostly unfacetted and unilamellar, a significant number of multilamellar vesicles were also present. Contrary to DMPG samples no uniform discs were observed. The size of the vesicles was consistent with the DLS measurements (~50-200 nm), and the bilayer thickness was 7±1 nm.

Irradiation Experiments.

When the ruthenium-functionalized vesicles (samples C and F) are irradiated with white light at 25° C., a gradual color change from yellow to red is observed. At any point of the experiment if the irradiation is stopped the spectrum of the solution also stops to evolve, which shows the thermal inertness of the ruthenium complex in the dark. FIG. 1a shows the evolution of the UV-visible spectrum of sample C as a function of irradiation time. Clear isosbestic points are observed at 458, 386, 332, 311, 297 and 288 nm, showing that a single photoreaction is taking place. The initial absorption band at 457 nm gradually vanishes to give rise to a new species characterized by an absorption band at 492 nm. The absorption spectrum in the end of the photoreaction is very close to that of sample B', in which $[Ru(terpy)(bpy)(OH_2)]^{2+}$ was added to vesicles functionalized with ligand 4 (see FIG. 1b). It is also close to that of $[Ru(terpy)(bpy)(OH_2)]^{2+}$ in water; we attribute the small differences between vesicle-containing and vesicle-free samples to the interaction between the aqua complex and the membrane. Similar results were obtained with DMPC vesicles: the UV-vis spectrum of sample F after irradiation was found nearly identical to that of sample E' (data not shown).

As shown in the insert of FIG. 1a, a pseudo first-order kinetics is observed for the photoreaction using white light $(\ln(C_t/C_0)=-k \times t)$, where $C_0$ and $C_t$ are the concentration of $[5]^{2+}$ before irradiation and after an irradiation time t, respectively). The quantum yield of the process was measured at 25° C. using monochromatic light set at the wavelength of the isosbestic point ($\lambda_{ex}$=452 nm). In the conditions of the experiment the quantum yield for the photosubstitution of 4 by an aqua ligand at the ruthenium center was found to be 0.0074(8) for DMPG and 0.0073(8) for DMPC vesicles.

Ultracentrifugation Experiments.

Samples C and F were subjected to ultracentrifugation, before and after irradiation. The absorbance of the supernatant was quantitatively measured at the absorption maximum of the ruthenium complex (454 nm before irradiation and 492 nm after), and compared to the absorbance before centrifugation (see Table 3).

With both DMPG and DMPC vesicles, the pellets obtained by ultracentrifugation before irradiation are yellow, and the absorbance of the supernatant low, thus showing attachment of the ruthenium complex to the lipid vesicles. After irradiation the situation is more contrasted (see Table 2 and Table 3): for anionic DMPG vesicles red pellets are observed, and according to the UV-visible spectrum of the supernatant only ~15% of the initial absorbance is retained. Thus, ~85% of the photochemically produced $[Ru(terpy)(bpy)(OH_2)]^{2+}$ complexes are contained in the pellet. On the contrary, for neutral DMPC vesicles the lipid pellets obtained after ultracentrifugation are colorless, and the absorbance at 492 nm is identical before and after centrifugation. Thus, in this case the released $[Ru(terpy)(bpy)(OH_2)]^{2+}$ is essentially non-interacting with the lipid bilayer.

For sample B' and E', after ultracentrifugation the pellets were found red and colorless, respectively (see Table 2), and the supernatant showed similarly low (16%) and high (75%) ruthenium content, which is comparable to sample C and F after irradiation (see Table 3). In all cases, a Rouser assay showed that the supernatant did not contain significant amounts of lipids, as the phosphate content was lower than 2% (see Table 3).

TABLE 2

Absorption maximum of the solution before ultracentrifugation, and color of the lipid pellets after centrifugation for samples A-F.[a]

| Sample | $\lambda_{max}$ of solution before ultracentrifugation (nm) | Color of pellet after ultracentrifugation |
|---|---|---|
| A, B | n.o. | Colorless[b] |
| B' | 492 | Red |
| C | 454 | Yellow |
| C irradiated | 492 | Red |
| D, E | n.o. | Colorless[b] |
| E' | 492 | Colorless[b] |
| F | 454 | Yellow |
| F irradiated | 492 | Colorless[b] |

[a]n.o. = not observed.
[b]The colorless pellets were not fully transparent and slightly diffused light.

TABLE 3

Percentages of immobilization of ruthenium at DMPG and DMPC vesicles before and after irradiation.

| Sample | Absorbance at $\lambda_{max}$ before centrifugation | Absorbance at $\lambda_{max}$ after centrifugation | Remaining Ru in supernatant[c] (%) | Remaining lipid in supernatant[d] (%) |
|---|---|---|---|---|
| A[a] | 0.292 | 0.050 | 17 | <0.8 |
| B' | 0.282 | 0.045 | 16 | <2.1 |
| C | 0.314 | 0.044 | 14 | <1.8 |
| C irradiated | 0.239 | 0.059 | 25 | <1.4 |
| D[a] | 0.273 | 0.283 | 103[b] | <0.3 |
| E' | 0.350 | 0.262 | 75 | <0.2 |
| F | 0.258 | 0.277 | 107[b] | <0.1 |
| F irradiated | 0.226 | 0.126 | 56 | <0.1 |

[a]Obtained by adding 1 mol % of $[Ru(terpy)(bpy)(OH_2)](BF_4)_2$ to sample A (A') or D (D').
[b]With DMPC samples (D', E', F and F irradiated) light scattering was found to be large, which significantly increased the absorbance of the baseline, hence the errors during application of the Beer-Lambert law. Estimated absolute errors on these values are 10-20%.
[c]According to UV-vis spectroscopy.
[d]According to Rouser assays.

Discussion

Typically, metal-steroid conjugates have been considered as protein targeting tools because steroids are protein substrates,[19-23] or for their ability to insert into biological membranes.[24-26] By covalently binding a 5α-cholestan-3β-ol fragment to a monodentate thioether ligand and subsequently coordinating ligand 4 to ruthenium, we aimed at decorating unilamellar vesicles with ruthenium polypyridyl complexes. UV=visible spectra of the functionalized DMPG and DMPC vesicles were comparable to the spectrum of $[5]^{2+}$ in acetone. In addition, the yellow color due to the presence of the sulfur-bonded ruthenium complex significantly diminished upon spinning down the lipid vesicles. Thus, we can conclude that the ruthenium complexes were attached to DMPG and DMPC membrane via 1) direct coordination of the sulfur atom to ruthenium, and 2) supramolecular insertion of the cholestanol moiety into the lipid bilayer.

Interestingly, a small (25%) to medium (56%) fraction of S-bound ruthenium complex was also found in the supernatant before irradiation for samples C and F, respectively. As a Rouser assay of the supernatant excludes small unilamellar vesicles that would not be spun down by centrifugation, such minor fraction might be caused by 1) partial hydrolysis of the ester bond in complex [5]$^{2+}$, which would liberate the partially water-soluble complex [Ru(terpy)(bpy)(S(Me)CH$_2$COOH)]$^{2+}$, or 2) exchange of the counter anion of complex [5]$^{2+}$. Indeed, the solubility of complex [5]$^{2+}$ in water highly depends on its counter anion. During the purification of compound [5]$^{2+}$ by chromatography for example, evaporation of acetone from the acetone/water/KNO$_3$ fractions ([NO$_3$]$^-$≈0.032 M) does not lead to precipitation of the orange complex, unless large amounts of saturated aqueous KPF$_6$ solution are added. Thus, compound [5]$^{2+}$ in the nitrate form, i.e., [5](NO$_3$)$_2$, is partly soluble in aqueous solution in spite of its long apolar tail, whereas [5](PF$_6$)$_2$ is not. Thus, the lipophilic hexafluorophosphate anions of the complex initially introduced in the vesicle-containing samples might gradually be exchanged by the more hydrophilic hydrogenophosphates or sulfates anions present in the buffer, thus increasing the solubility of complex [5]$^{2+}$ in aqueous solution, which might explain the amount of complex still present in the supernatant after centrifugation.

The photochemistry of [Ru(terpy)(N$_1$—N$_1$)(Y)]$^{2+}$, where N$_1$—N$_1$ is a bidentate imine ligand and Y is a monodentate ligand, has been studied thoroughly in (wet) organic solvents.[27-31] We study here the selective photosubstitution of Y by an aqua ligand in purely aqueous solution. The presence of clear isosbestic points during irradiation shows that a single photoreaction is taking place. The first-order kinetics also correspond to previous work, where it was shown that upon ligand photoexpulsion coordination of a solvent molecule is taking place.[32] UV-vis spectroscopy, TEM, and centrifugation experiments all converge to a great similarity between samples C after irradiation and sample B' on the one hand, and between sample F after irradiation and sample E' on the other hand (see Table 1). Thus, we conclude that the following reaction is taking place at the membrane:

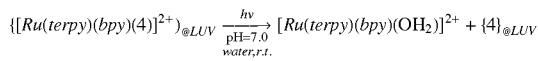

As the cholestanol fragment of ligand 4 is inserted in the membrane, the above reaction should lead to the detachment of the ruthenium complex from the bilayer. Quantum yield measurements show that the efficiency of the photocleavage of the ruthenium complexes from the vesicles is similar to related homogeneous systems,[27, 32] and according to DLS and cryo-TEM analysis it does not change the size or shape of the vesicles themselves.

Example 2

Experimental Section

Synthesis.

AgPF$_6$, N-acetyl-L-methionine, D-biotin, L-methionine, and 2-methylthioethan-1-ol were purchased from Sigma-Aldrich and used as such. All manipulations for the synthesis of [6](Cl)$_2$, [7](Cl)$_2$, [8](Cl)$_2$ and [9](Cl)$_2$ were performed in the absence of light. For NMR spectra a Bruker 300 MHz NMR spectrometer was used, for ES MS a Thermoquest Finnagen AQA spectrometer and for UV-Vis measurements a Cary Varian UV-Visible spectrometer. [Ru(tpy)(bpy)(H$_2$O)](PF$_6$)$_2$ was synthesised according to a modified literature procedure:[13] [Ru(tpy)(bpy)(Cl)](Cl)[13] (150 mg, 0.267 mmol) and AgPF$_6$ (135 mg, 0.534 mmol) were dissolved in acetone/water (3:1, 20 mL). The reaction mixture was refluxed under argon for 2 hours at 80° C. The white suspension was filtered hot over celite. The acetone was slowly evaporated with a rotary evaporator under vacuum, which led to precipitation of [Ru(tpy)(bpy)(H$_2$O)](PF$_6$)$_2$. The suspension was put in the fridge for 4 days to ensure complete precipitation. Yield: 66% (141 mg, 0.177 mmol).

Compound [6](Cl)$_2$:

[Ru(tpy)(bpy)(Cl)](Cl) (200 mg, 0.356 mmol) and N-acetyl-L-methionine (68.1 mg, 0.356 mmol) were dissolved in distilled water (20 mL). The reaction mixture was refluxed under argon for one day at 80° C. Water was evaporated under vacuum with a rotary evaporator at 70° C. Compound [6](Cl)$_2$ was purified by column chromatography (silica, acetone/H$_2$O/HCl (1M), 16:4:1). The acetone was evaporated under vacuum with a rotary evaporator at 30° C. Water and HCl were removed by freeze-drying. Finally, the complex was recrystallised from MeOH/Et$_2$O as an orange powder. Yield: 56% (151 mg, 0.201 mmol). $^1$H-NMR (300 MHz, CD$_3$OD, 298 K), δ (ppm): 9.93-9.74 (m, J=7.1 Hz, 1H, H1), 8.95-8.74 (m, 3H, H4+H17), 8.73-8.50 (m, J=14.7, 8.0 Hz, 3H, H14+H7), 8.51-8.32 (m, 2H, H18+H3), 8.22-8.02 (m, 3H, H13+H2), 7.95 (td, J=8.2, 1.6 Hz, 1H, H8), 7.85-7.71 (m, 2H, H11), 7.47 (ddt, J=7.6, 5.4, 1.1 Hz, 2H, H12), 7.34-7.13 (m, 2H, H10+H9), 4.38 (dd, J=9.1, 4.9 Hz, 1H, H22), 2.01-1.84 (m, 3H, H19 or H25), 1.87-1.55 (m, 4H, H20+H21), 1.44-1.29 (m, 3H, H19 or H25). $^{13}$C-NMR (300 MHz, CD$_3$OD, 298 K), δ (ppm): 172.09 (C23 or C24), 158.35+157.75+157.13+156.99 (C5+C6+C15+C16), 153.36 (C11), 152.35 (Cl), 149.73 (C10), 139.20 (C13), 138.56 (C8), 138.49+137.29 (C3+C18), 128.82 (C12), 128.09 (C2), 127.44 (C9), 125.34+124.96 (C7+C14), 124.53+124.18 (C4+C17), 50.57 (C22), 30.31+28.59 (C20+C21), 21.49+13.22 (C19+C25). ES MS m/z (calc): 680.95 (680.77 [M-2Cl—H]$^+$), 526.01 (525.59 [M-2Cl-bpy]$^+$), 348.82 (348.40 [M-2Cl+CH$_3$]$^{2+}$), 261.41 (261.28 [M-2Cl—N-acetylmethionine+MeOH]$^{2+}$), 245.61 (245.26 [M-2Cl—N-acetylmethionine]$^{2+}$). UV-vis: λ$_{max}$ (ε in L·mol$^{-1}$·cm$^{-1}$) in H$_2$O: 452 nm (5.35×10$^3$).

Compound [7](Cl)$_2$:

[Ru(tpy)(bpy)(Cl)](Cl) (200 mg, 0.356 mmol) and D-biotin (87.0 mg, 0.356 mmol) were dissolved in distilled water (30 mL). The reaction mixture was refluxed under argon for one day at 80° C. Water was evaporated under vacuum at 70° C. with a rotary evaporator. Compound [7](Cl)$_2$ was purified by column chromatography (silica gel, acetone/H$_2$O/HCl (1M), 16:4:1). Acetone was evaporated under vacuum with a rotary evaporator at 30° C. Water and HCl were removed by freeze-drying. Finally, the complex was recrystallised from EtOH/Et$_2$O as an orange powder. Yield: 32% (92.0 mg, 0.114 mmol). $^1$H-NMR (300 MHz, CD$_3$OD, 298K), δ (ppm): 9.87 (d, J=5.1 Hz, 1H, H1), 8.88 (d, J=8.1 Hz, 3H, H4+H17), 8.78-8.55 (m, 3H, H14+H7), 8.56-8.32 (m, 2H, H18+H3), 8.11 (dd, J=16.4, 7.6 Hz, 3H, H13+H2), 7.95 (dd, J=14.1, 6.0 Hz, 2H, H8+H11 or H11'), 7.81 (d, J=4.9 Hz, 1H, H11 or H11'), 7.48 (dd, J=12.4, 6.8 Hz, 2H, H12+H13), 7.26 (d, J=8.1 Hz, 2H, H10+H9), 4.18 (s, 2H, H19 or H27), 2.34 (d, J=9.0 Hz, 1H, H20 or H22 or H23), 2.27-2.07 (m, 2H, H19 or H27), 1.91 (t, J=19.9 Hz, 1H, H20 or H22 or H23), 1.78 (d, J=10.4 Hz, 1H, H20 or H22 or H23), 1.54-0.97 (m, 6H, H24+H25+H26). $^{13}$C-NMR (300 MHz, CD$_3$OD, 298K), δ (ppm): 159.56, 159.35, 158.65, 158.58, 158.14, 158.09, 154.85, 154.46, 153.15, 150.68, 140.51, 140.47, 139.82, 139.69, 138.63, 129.88, 129.76, 129.09, 128.61, 126.67, 126.50, 126.21, 125.92, 125.83, 125.32, 60.25, 58.56, 57.55, 40.65, 34.16, 28.12, 27.82, 25.39. ES MS m/z (calc): 748.94 (748.86 [M-2Cl—H+CH$_3$]$^+$), 525.97 (525.98 [M-Cl-biotin]$^+$), 374.64 (374.43 [M-2Cl—H+CH$_3$]$^{2+}$), 261.39 (261.28 [M-2Cl-biotin+MeOH]$^{2+}$), 245.13 (245.26 [M-2Cl$^-$-biotin]$^{2+}$), 244.03 (244.31 [biotin]$^+$). UV-vis: $\lambda_{max}$ ($\epsilon$ in L·mol$^{-1}$·cm$^{-1}$) in H$_2$O: 444 nm (5.01×10$^3$).

Compound [8](BF$_4$)$_2$:

[Ru(tpy)(bpy)(OH$_2$)](BF$_4$)$_2$ (68 mg, 0.100 mmol) and L-methionine (16.5 mg, 0.110 mmol) were dissolved in distilled water (30 mL). The reaction mixture was heated under argon for two days at 80° C., cooled down to room temperature and filtered under celite. Compound [8](Cl)$_2$ was purified by high performance liquid chromatography using water/methanol as eluents. The first fractions were collected, and the solvents were removed by rotavap (methanol) and freeze-drying (water) to yield 45 mg of an orange-red solid. Yield: 82%. $^1$H NMR (400 MHz, CD$_3$OD) δ (ppm): 9.86 (d, J=5.5 Hz, 1H), 8.84 (d, J=8.2 Hz, 1H), 8.80 (d, J=8.1 Hz, 2H), 8.65 (d, J=8.1 Hz, 2H), 8.62 (d, J=8.3 Hz, 1H), 8.41 (td, J=8.0, 5.1 Hz, 2H), 8.15-8.06 (m, 3H), 7.98-7.91 (m, 1H), 7.79 (d, J=5.5 Hz, 2H), 7.49-7.43 (m, 2H), 7.28 (d, J=4.7 Hz, 1H), 7.26-7.21 (m, 1H), 1.92-1.80 (m, 3H, CH+CH$_2$S), 1.73 (m, 2H, CH$_2$), 1.37 (s, 3H, MeS). $^{13}$C NMR (101 MHz, CD$_3$OD) δ (ppm): 174.86 (s), 158.11 (d, J=1.1 Hz), 157.56 (s), 157.03 (s), 156.69 (s), 153.13 (s), 152.55 (s), 149.49 (s), 139.03 (d, J=2.7 Hz), 138.23 (d, J=3.1 Hz), 137.11 (s), 128.64 (d, J=1.5 Hz), 128.06 (s), 127.18 (s), 125.16 (s), 124.66 (s), 124.33 (s), 123.94 (s), 53.64 (s), 30.46 (s), 29.82 (s), 12.98 (s). High resolution ES MS m/z (calc): 320.0543 (320.0597 [M-2BF$_4$]$^{2+}$).

Compound [9](BF$_4$)$_2$:

[Ru(tpy)(bpy)(OH$_2$)](BF$_4$)$_2$ (35 mg, 0.052 mmol) and 2-methylthioethan-1-ol (44 mg, 0.447 mmol) were dissolved in distilled water (6 mL). The reaction mixture was heated under argon overnight (16 h) at 80° C., cooled down to room temperature and freeze-dried. The excess of ligand was washed away with diethylether to quantitatively afford compound [9](BF$_4$)$_2$ as an orange solid. $^1$H NMR (400 MHz, D$_2$O) δ (ppm): 9.81 (d, J=5.4 Hz, 1H), 8.70 (d, J=8.1 Hz, 1H), 8.66 (d, J=8.2 Hz, 2H), 8.50 (d, J=8.1 Hz, 2H), 8.44 (d, J=8.2 Hz, 1H), 8.36 (t, J=8.1 Hz, 2H), 8.03 (dd, J=14.5, 6.7 Hz, 3H), 7.88 (t, J=8.2 Hz, 1H), 7.81 (d, J=5.3 Hz, 2H), 7.42-7.31 (m, 2H), 7.28 (d, J=5.5 Hz, 1H), 7.11 (t, J=7.0 Hz, 1H), 3.45 (t, J=5.7 Hz, 2H, CH$_2$O), 1.83 (t, J=5.7 Hz, 2H, CH$_2$S), 1.36 (s, 3H, SMe).

Complex Stability Measurements at Human Body Temperature.

[Ru(terpy)(bpy)(Cl)](Cl) (2.23 mg, 3.97 µmol), compound [6](Cl)$_2$ (2.14 mg, 2.84 µmol) and compound [7](Cl)$_2$ (2.18 mg, 2.71 µmol) were weighed separately into three different NMR tubes. D$_2$O (0.80 mL) was added to each of the NMR tubes and $^1$H NMR spectra were taken. The NMR tubes were put into closed pressure tubes and kept in the dark at 37° C. to check the stability of the Ru—Cl and Ru—S bond. $^1$H NMR spectra of each of the tubes were taken after 4 hours, 1 day, 3 days and 3 weeks. The NMR tubes were kept in an ice bath during transport in order to temporarily freeze the reaction. In the case of [Ru(terpy)(bpy)(Cl)](Cl), an equilibrium had been reached after four hours, characterized by 10% of [Ru(terpy)(bpy)(Cl)](Cl) and 90% of [Ru(terpy)(bpy)(H$_2$O)](Cl)$_2$. The bond between ruthenium and the sulfur atom proved to be much more stable. After three weeks, compound [6](Cl)$_2$ had not been converted to [Ru(terpy)(bpy)(H$_2$O)](Cl)$_2$ at all. For compound [7](Cl)$_2$, no changes were observed after the first day. After three days, however, there was a few percent of [Ru(terpy)(bpy)(H$_2$O)](Cl)$_2$. After three weeks at 37° C., the ratio between compound [7](Cl)$_2$ and [Ru(terpy)(bpy)(H$_2$O)](Cl)$_2$ was 7:3.

Photochemical Quantum Yield Determination in Homogeneous Conditions.

A Cary Varian UV-Visible spectrometer was used for measuring UV-visible spectra. All sample preparations were performed under deemed light, protecting sample from light by aluminium foil. For irradiation, a LOT 1000 W Xenon arc lamp, fitted with a water filter and an interference filter (452 nm, $\lambda_{1/2}$=20 nm, Andover 450F510-50), was used. In these conditions, the photon flux was measured by standard potassium ferrioxalate actinometry[14] to be 5.94×10$^{-8}$ einstein·s$^{-1}$. A 1.0 ml volume of a 0.50 mM solution of compound [6](Cl)$_2$ or [7](Cl)$_2$ in deionized water was transferred with a pipette into a quartz cuvette with a path length of 1.00 cm, and 2.0 mL of water was added. A first spectrum was taken between 400 nm and 600 nm in order to determine the extinction coefficient. Then, the sample was irradiated for 10 minutes and after each minute of irradiation a UV-vis spectrum was taken between 400 nm and 600 nm. Finally, the sample was irradiated for an additional 60 and 75 minutes in order to achieve a photochemical steady state and verify the two last spectra were identical. The time evolution of the advancement n/n$_0$ of the photochemical reaction was calculated; a linear regression of ln(n/n$_0$)=f(t) afforded the quantum yield of the photoreaction; the final numerical values are 0.018(4) for compound [6](Cl)$_2$ and 0.011(3) for compound [7](Cl)$_2$.

Results

Complex Formula and Synthesis.

Scheme 8 shows the chemical structures of compounds [6](Cl)$_2$, [7](Cl)$_2$, [8](BF$_4$)$_2$, and [9](BF$_4$)$_2$. [Ru(terpy)(bpy)(N-acetyl-L-methionine)](Cl)$_2$ (compound [6](Cl)$_2$) and [Ru(terpy)(bpy)(D-biotin)](Cl)$_2$ (compound [7](Cl)$_2$) are synthesised by directly reacting [Ru(terpy)(bpy)(Cl)](Cl) with the corresponding thioether ligand in water at 80° C., followed by chromatography separation on silica gel. Thus, due to the stronger Ru—S bond compared to Ru—Cl in water there is no need to trap the chloride ions with silver salts. [Ru(terpy)(bpy)(L-methionine)](BF$_4$)$_2$ (compound [8](BF$_4$)$_2$) and [Ru(terpy)(bpy)(mte)](BF$_4$)$_2$ (compound [9] (BF$_4$)$_2$, mte=2-methylthioethan-1-ol) were synthesized by the conventional method, which consists in heating [Ru(terpy)(bpy)(OH$_2$)](BF$_4$)$_2$ and the corresponding ligand in water at 80° C. Compound [8](BF$_4$)$_2$) was purified by HPLC using water/methanol mixtures as eluent. Compound [9](BF$_4$)$_2$ was freeze-dried and washed with diethylether to remove the excess of 2-methylthioethan-1-ol.

Scheme 8.
Formula of compounds [6](Cl)₂, [7](Cl)₂, [8](BF₄)₂, and [9](BF₄)₂.

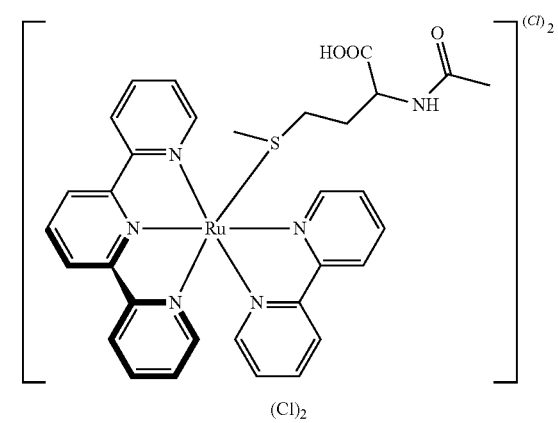

[6](Cl)₂

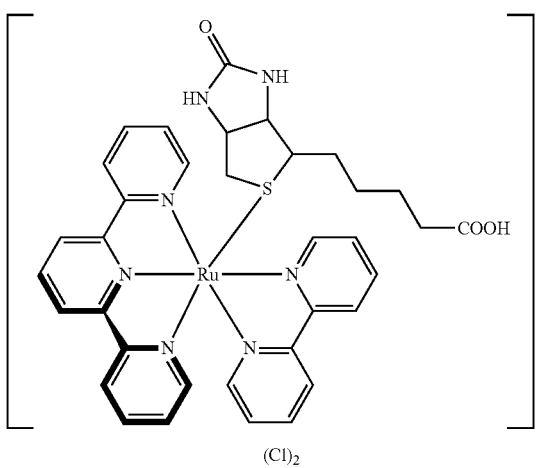

[7](Cl)₂

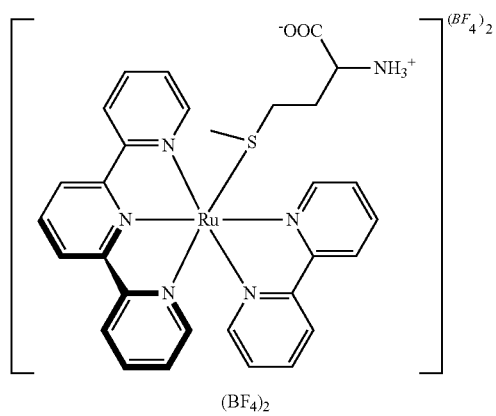

[8](BF₄)₂

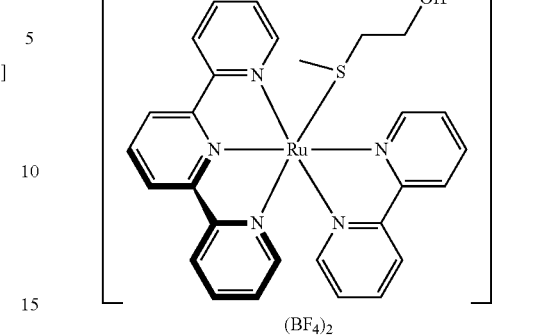

[9](BF₄)₂

The monodentate sulfur ligand of compounds [6](Cl)₂, [7](Cl)₂, [8](BF₄)₂ and [9](BF₄)₂ is photosubstituted by an aqua ligand upon irradiation with white light in aqueous solution:

[Ru—SRR']²⁺→[Ru—OH₂]²⁺+SRR'

According to the stability measurements of compounds [6](Cl)₂ and [7](Cl)₂ in water, this substitution reaction does not take place thermally at body temperature within a day when SRR' is D-biotin or N-acetyl-L-methionine. The photosubstitution quantum yields were determined to be 0.018(4) for compounds [6](Cl)₂ and 0.011(3) for compounds [7](Cl)₂, using monochromatic blue light (excitation at 452 nm).

Discussion

Water-soluble thioether ligands such as L-methionine and 2-methylthioethan-1-ol (mte) react cleanly with [Ru(terpy)(bpy)(OH₂)](BF₄)₂ in water to afford the corresponding compounds [8](BF₄)₂ and [9](BF₄)₂. With L-methionine, removal of the highly polar amino acid is difficult and requires HPLC separation, leading to lower preparative yields.

With mte however, simple washing of the crude mixture with diethylether allows complete removal of the excess of ligand to afford [9](BF₄)₂ quantitatively. Alternatively, it is also possible to directly react the chlorido compound [Ru(terpy)(bpy)(Cl)](Cl) with thioether ligands, as the Ru—Cl bond is labile in water whereas the Ru—S bond is not. Thus, compounds [6](Cl)₂ and [7](Cl)₂ are synthesised by directly reacting [Ru(terpy)(bpy)(Cl)](Cl) with the corresponding thioether ligand in water at 80° C. overnight. Separation of the sulfur-bonded ruthenium product from the starting materials is achieved by column chromatography on silica gel using acetone/water/HCl mixtures as eluent. Acetone should be removed with a rotary evaporator, and water and hydrochloric acid by freeze-drying. Reprecipitation from methanol/diethylether is necessary to completely remove the last traces of HCl. The preparative yield was 56% for compound [6](Cl)₂ and 32% for compound [7](Cl)₂. The lower yield for compound [7](Cl)₂ might be explained by the higher steric hindrance of biotin. In situ ¹H NMR studies show that it is possible to get 100% conversion in both cases if a five times excess of ligand is used. In this case, the reaction is also finished more quickly. However, it is more difficult to isolate the ruthenium compound from the excess of ligand.

Compound [7](Cl)₂ is obtained as a single isomer, but compound [6](Cl)₂ seem to appear as a mixture of a major and a minor isomer. The ¹H NMR spectrum shows two partially overlapping A2 doublet with one major and one minor species (see Scheme 7 for NMR notation of the bpy ligand). Mass spectrometry does not show any sign of ruthenium-bound sulfoxide or ruthenium-methionine complex with an hydrolyzed acetyl group, so that the minor species must correspond to an isomer of the main product. N-acetylmethionine might also coordinate through the oxygen atom of the carboxylic acid group to ruthenium. However, biotin should show the same feature as it also has an acid group. As it is not the case, the chirality of N-acetylmethionine has to be considered: two diastereomers are formed when each of the two diastereotopic lone pairs of the sulfur atom coordinates to ruthenium. This explanation accounts for the very similar chemical shift of the A2 protons for both species by $^1$H NMR (see FIG. 2), which suggests chemically very similar monodentate ligands. DFT calculations predict an energy difference of 12.5 kJ·mol$^{-1}$ for both diastereoisomers, which is consistent with a few percent of the minor isomer, thus to the experiment. Although biotin is also chiral, the energy difference between both possible isomers of [7](Cl)$_2$ was calculated to be 35.1 kJ·mol$^{-1}$, i.e., there is virtually one isomer only in that case. Stereoselective coordination of D-biotin to first-row transition metal complexes has been suggested by Sigel et al.[33]

The thermal stability of compound [6](Cl)$_2$ and compound [7](Cl)$_2$ in water is very important, since this invention focuses on using monodentate thioethers as inorganic protecting groups, which can be selectively removed by irradiation. The thermal instability of Ru—Cl in aqueous solution is known. After a few hours at 37° C. an equilibrium was reached, characterised by 10% of [Ru(terpy)(bpy)(Cl)](Cl) and 90% of [Ru(terpy)(bpy)(OH$_2$)](Cl)$_2$. Compound [6](Cl)$_2$ and [7](Cl)$_2$ are both a lot more stable at human body temperature than [Ru(terpy)(bpy)(Cl)](Cl). After three weeks at 37° C. in aqueous solution, compound [6](Cl)$_2$ shows no trace of [Ru(terpy)(bpy)(OH$_2$)](Cl)$_2$, whereas compound [7](Cl)$_2$ liberated a few percents of [Ru(terpy)(bpy)(OH$_2$)](Cl)$_2$. Since the general residence time of a drug in the body is 24 to 48 hours, the amount of thermally released aqua complex is negligible, and biotin can also be used as a thermally stable inorganic protecting group for ruthenium-based polypyridyl anticancer complexes.

Example 3

Replacing a Weakly Bound Chloride Ligand by a Strongly Bound Sulphur Ligand Diminishes the Cytotoxicity of Ruthenium Polypyridyl Compounds in the Dark HepG2 cancer cells were grown in RPMI 1640 medium containing (−) L-glutamine at 37° C. and in an atmosphere of 95% O$_2$ and 5% CO$_2$. [Ru(tpy)(bpy)Cl]Cl or [Ru(tpy)(bpy)(AMet)]Cl$_2$ (compound [7](Cl)$_2$) was added to the cells and incubated for 30 min in the dark (concentration: 1.7 mM), after which a WST-1 cell viability test (normalized to protein content) was performed on each well. The cell survival was reduced by 49% in presence of [Ru(tpy)(bpy)Cl]Cl, whereas it was not reduced (within experimental errors) in presence of compound [7](Cl)$_2$. In this experiment, the difference in water solubility between the chlorido and thioether complexes might also play a role, as uptake might be different for both compounds.

Example 4

Compound 10.

Cholesterol (200 mg, 0.52 mmol) and N-acetyl-L-methionine (100 mg, 0.52 mmol) were dissolved in anhydrous benzene (10 mL) under argon atmosphere. DCC (140 mg, 0.68 mmol) and DMAP (2 mg, 0.02 mmol, 3%) were added and the mixture was stirred vigorously for 12 hours, after which the solution was filtered to remove insoluble materials. The solvent was evaporated under vacuum by rotary evaporation at 30° C. The crude product was purified by column chromatography on silica gel (petroleum ether/EtOAc, 70:30). The solvents were evaporated by rotary evaporation at 30° C., and compound 10 was obtained as a white sticky solid. Yield: 50% (150 mg, 0.26 mmol). $^1$H NMR (300 MHz, CDCl$_3$) δ 6.13 (d, J=8.18 Hz, 1H, δ), 5.38 (d, J=4.09 Hz, 1H, 6), 4.70-4.64 (m, 3H, 3, γ), 3.44 (m, 1H, ε), 2.33 (m, 2H, β), 2.10 (s, 3H, α), 2.03 (s, 2H, 4). $^{13}$C NMR (75 MHz, CDCl$_3$) δ 171.70 (Cχ), 169.96 (Cη), 139.30 (C5), 125.31, 123.18 (C6), 75.65 (C3), 56.79, 56.24, 51.90 (Cγ), 50.11, 49.66, 42.42, 39.81, 39.62, 38.11, 38.07 (Cβ), 36.98, 36.68, 36.29, 35.89, 37.70, 33.73, 32.22, 32.01, 31.93 (Cα), 30.05, 29.81, 28.33, 28.12, 27.82, 27.79, 25.60, 24.93, 24.83, 24.38, 23.93, 23.36, 22.93, 22.67, 21.14 (C4), 19.42, 18.83, 18.74, 15.67, 11.96. ES MS m/z (calc): 560.1 (560.4, [M+H]$^+$), 369.2 (369.4, [M-AMet]$^+$). Elemental analysis (%) for C$_{34}$H$_{57}$NO$_3$S+H$_2$O: C, 70.66; H, 10.30; N, 2.43, S, 5.54. found: C, 70.45; H, 9.99; N, 2.99; S, 5.46.

Compound [11](BF$_4$)$_2$:

[Ru(terpy)(azpy)(Cl)](Cl) (35 mg, 0.06 mmol), ligand 10 (50 mg, 0.09 mmol) and AgBF$_4$ (25 mg, 0.13 mmol) were dissolved in anhydrous acetone (20 mL) in the dark. The mixture was refluxed under argon for 48 hours. The solution was then filtered over celite to remove insoluble materials. The solvent was evaporated under vacuum by rotary evaporation at room temperature. The complex was purified by column chromatography on silica gel (DCM/MeOH 80:20). The solvent was evaporated under vacuum by rotary evaporation at 35° C. Finally, [11](BF$_4$)$_2$ was reprecipitated from MeOH/Et$_2$O as a purple solid. Yield: 9% (7 mg, 0.005 mmol). $^1$H NMR (300 MHz, Acetone) δ 9.90 (d, J=6.25 Hz, 1H, 6A), 9.06 (d, J=8.75 Hz, 1H, 3A), 8.74-8.65 (m, 5H, 5T, 3T', 5A), 8.44-8.30 (m, 4H, 4A, 4T', 4T), 7.81 (m, 2H, 6T), 7.67 (m, 2H, 3T), 7.32 (m, 1H, 12A), 7.19-7.11 (m, 3H, 11A, 13A, 6), 6.35 (d, J=8.75 Hz, 2H, 10A, 14A), 5.34 (s, 2H, 4), 4.43-4.36 (m, 3H, γ, β). UV-vis: λ$_{max}$ in nm (ε in L·mol$^{-1}$·cm$^{-1}$) in CHCl$_3$: 509 nm (7980). ES MS m/z (calc): 1164.7 (1164.5, [M-(BF$_4$)]$^+$), 708.1 (708.1, [M-cholesterol-2(BF$_4$)]$^{2+}$), 605.0 (605.1, [M-L-(BF$_4$)]$^+$), 538.8 (538.8, [M-2(BF$_4$)]$^{2+}$).

Compound [12](PF$_6$)$_2$:

[Ru(terpy)(bpy)(Cl)](Cl) (45 mg, 0.08 mmol) and AgBF$_4$ (30 mg, 0.15 mmol) were dissolved in anhydrous acetone (20 mL) in the dark. The mixture was refluxed under argon for 1 hour. Ligand 10 (70 mg, 0.12 mmol) was added and the mixture was refluxed under for 48 hours. The solution was filtered hot over celite to remove insoluble materials. The solvent was evaporated under vacuum by rotary evaporation at room temperature. The complex was purified by column chromatography on silica gel (Acetone/H$_2$O/KPF$_6$, 100:10: 1.5, second band, R$_f$=0.28). The acetone was evaporated under vacuum at 30° C., upon which the product [12](PF$_6$)$_2$ precipitated as an orange solid. Finally [12](PF$_6$)$_2$ was filtered, washed with water and dried under vacuum at 40° C. Yield: 28% (30 mg, 0.022 mmol). $^1$H NMR (300 MHz, Acetone-$d_6$) δ 9.98 (d, J=7.5 Hz, 1H, 6A), 8.95 (m, 3H, 3T', 3A), 8.78 (d, J=7.5 Hz, 2H, 6T), 8.71 (d, J=7.5 Hz, 1H, 6B), 8.56-8.47 (m, 2H, 4T', 4A), 8.23-8.13 (m, 3H, 5T, 5A), 8.04-8.00 (m, 3H, 3T, 5B), 7.57-7.54 (m, 3H, 3B, 4T), 7.31 (m, 1H, 4B), 7.17 (d, J=7.5, 1H, δ), 5.35 (m, 1H, 6), 4.45-4.42 (m, 2H, γ, 3). $^{13}$C NMR (75 MHz, Acetone) δ 171.21 (Cχ), 170.47 (Cη), 159.01, 158.43, 157.79, 157.67, 154.43, 154.41, 153.35, 151.01, 140.40 (C5), 139.99, 139.95, 139.24, 139.19, 138.05, 129.60, 129.56, 128.90, 128.25, 126.06, 125.68, 125.35, 124.84, 123.46 (C6), 75.67 (C3), 57.57, 57.06, 51.32 (Cγ), 51.01, 43.11, 40.61, 40.26, 38.68 (Cβ), 37.66, 37.33, 36.96, 36.59, 32.70 (Cα), 32.59, 31.12, 30.61, 28.69, 28.35, 24.92, 24.53, 23.07, 22.83, 21.74 (C4), 19.65, 19.14, 14.04, 12.23. UV-vis: $\lambda_{max}$ in nm (ε in L·mol$^{-1}$·cm$^{-1}$) in CHCl$_3$: 460 nm (8310). ES MS m/z (calc): 1195.9 (1195.4, [M-PF$_6$]$^+$), 681.2 (681.1, [M-(Cholest-5-en)-2(PF$_6$)]$^+$), 525.7 (525.2, [M-2(PF$_6$)]$^{2+}$).

Compound [13](Cl)$_2$:

[Ru(terpy)(apy)(Cl)](Cl) (100 mg, 0.170 mmol) and N-acetyl-L-methionine (169 mg, 0.867 mmol) were dissolved in water (40 mL). The reaction mixture was heated with stirring under argon for 2 hours at 80° C. H$_2$O was removed by freeze drying. The complex was purified by chromatography column (silica, acetone/H$_2$O/HCl (1M), 16:4:1). Acetone was evaporated under vacuum at 25° C. H$_2$O and HCl were removed by freeze drying. Compound [13](Cl)$_2$ was reprecipitated from MeOH/Et$_2$O and obtained as a purple solid. Yield: 35% (46.0 mg, 0.059 mmol). $^1$H NMR (300 MHz, D$_2$O, 298 K): δ (ppm): 9.77 (d, J=5.6 Hz, 1H, 6A), 8.99 (d, J=7.8 Hz, 1H, 3A), 8.55 (t, J=7.2 Hz, 1H, 4A), 8.44 (t, J=6.3 Hz, 4H, 3T, 3T'), 8.28 (m, 2H, 5A, 4T'), 8.13 (t, J=7.8 Hz, 2H, 4T), 7.94 (d, J=3.6 Hz, 1H), 7.90 (t, J=7.1 Hz, 1H, 6A'), 7.66 (m, 1H, 4A'), 7.50 (m, 4H, 5T, 6T), 7.32 (m, 1H, 5A'), 6.99 (d, J=8.0 Hz, 1H, 3A'), 4.02 (s, 1H, ε), 1.88 (s, 3H, φ), 1.78-1.57 (m, 4H, γ, β, δ), 1.53 (s, 3H, α). $^{13}$C NMR (75 MHz, D$_2$O) δ 174.73, 173.67, 165.46, 161.21, 157.44, 155.17, 153.64, 152.62, 149.99, 148.44, 140.49, 140.48-139.55, 138.56, 129.94, 129.53, 128.72, 128.71-127.77, 125.88, 125.01, 124.17, 123.83, 123.01, 115.63, 50.98, 29.85, 27.62, 21.78, 13.86. ES MS m/z: 554.0 (554.0 [M-L-Cl]$^+$), 261.5 (259.3 [M-L-2Cl$^-$]$^{2+}$).

Scheme 9. Chemical structure and atom numbering for compounds 10, [11](BF$_4$)$_2$, and [12](PF$_6$)$_2$, and [13](Cl)$_2$.

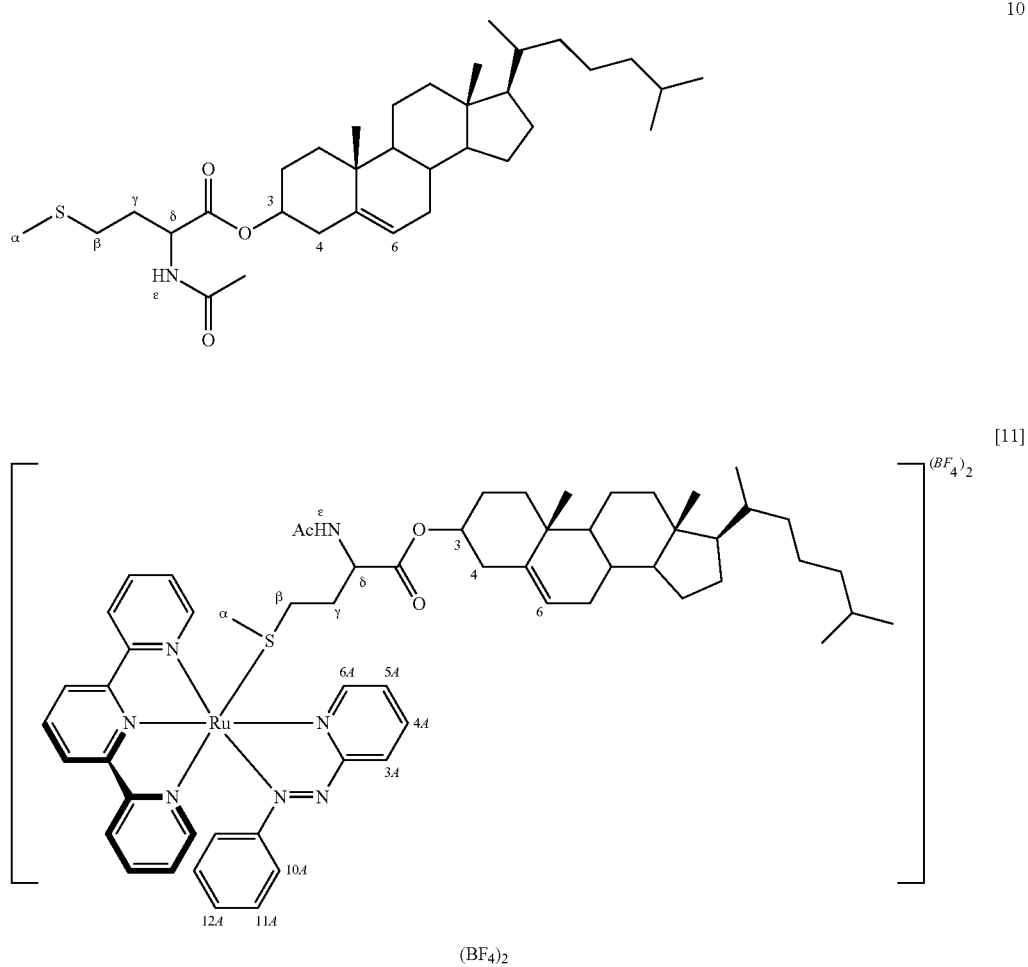

-continued

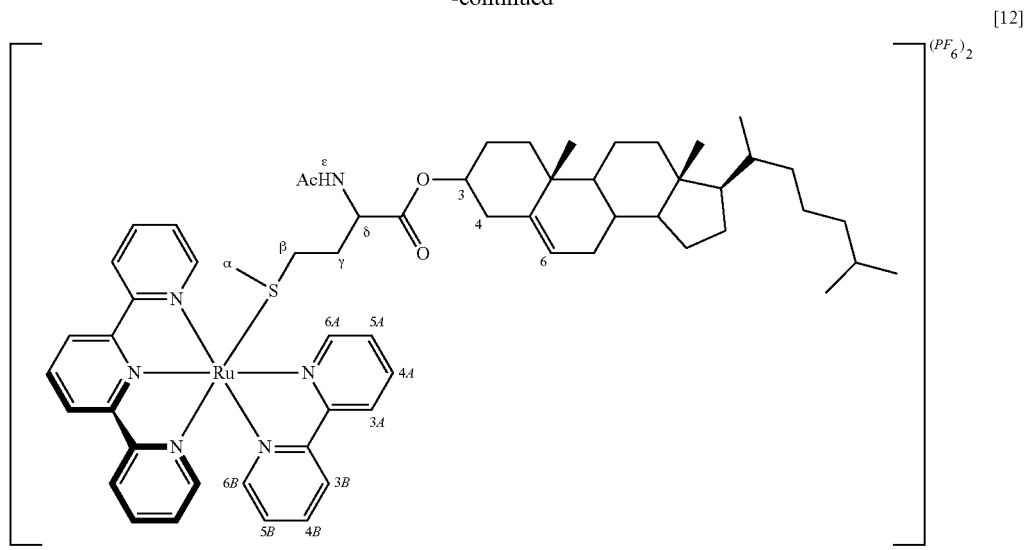

[12]

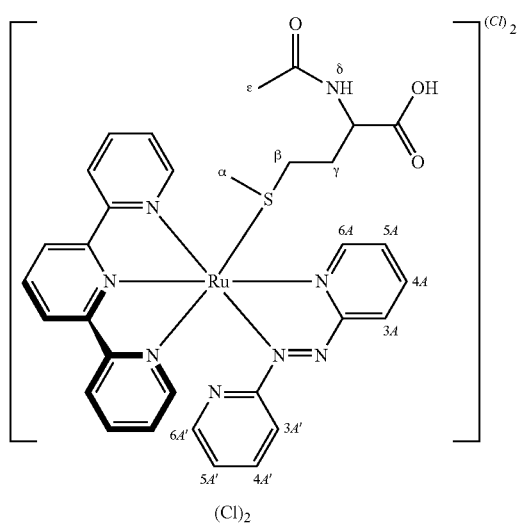

[13]

Example 5

Thermal Stability of the Ru—S Bond of [13](Cl)₂ in the Dark Compared to that of the Ru—Cl Bond

The Thermal Stability of the Ru—S Bond in the Dark is a Critical Parameter of the Proposed New Compounds, as a Stable Ru—S Bond Means a Drug that Cannot Coordinate to DNA or Proteins, Thus a Drug that Will have a Lower Toxicity.

The stability of the Ru—S bond was measured at human body temperature and in the dark. To do so, compound [Ru(tpy)(apy)Cl]Cl, and [Ru(tpy)(apy)(AMet)]Cl$_2$, (compound [13](Cl)$_2$) were dissolved in D$_2$O and kept in the dark at 37° C. The release of the aqua species was measured by $^1$H NMR after 4 hours, 1 days, and 3 weeks. As seen in Table 4, after 4 hours there is no sign of cleavage of the Ru—S bond for both thioether compounds, whereas for its chlorido precursor the equilibrium between [Ru—Cl] and [Ru—OH$_2$] is already reached. The stability of the Ru—S bond depends on the nature of the polypyridyl ligands (see Example 2), but in general it is much higher than that of the Ru—Cl bond.

TABLE 4

Conversion (%) of Ru compounds into their aqua complexes in. D$_2$O in the dark (T = +37° C.).

| Compound/Time | Bond | 4 h | 1 day | 3 weeks |
|---|---|---|---|---|
| [Ru(tpy)(apy)(Cl)](Cl) | Ru—Cl | 48 | 48 | 48 |
| [Ru(tpy)(apy)(AMet)](Cl)$_2$ | Ru—S | 0 | 21 | 46 |

The Ru—S Bond of [13](Cl)$_2$ can be Cleaved by Visible Light Irradiation

As shown in Example 2 visible light irradiation of [Ru(tpy)(bpy)(AMet)]Cl$_2$ (compound [6](Cl)$_2$) or [Ru(tpy)(bpy)(biotin)]Cl$_2$ (compound [7](Cl)$_2$) cleaves the Ru—S bond, thus releasing the free AMet or biotin ligand and the aqua complex [Ru((tpy)(bpy)(OH$_2$)]$^{2+}$. Similarly, $^1$H NMR studies realized for [Ru(tpy)(apy)(AMet)]Cl$_2$ show that the initial doublet observed at 9.77 ppm (in D$_2$O) is gradually converted upon visible light irradiation into doublets at 9.80 and 9.54 ppm, characteristic for [Ru(tpy)(apy)(Cl)]$^+$ and [Ru(tpy)(apy)(OH$_2$)]$^{2+}$, respectively. Thin layer chromatography (eluent: acetone:water:HCl mixture) also concludes to the total disappearance of the starting compound. Thus, the ruthenium-sulfur bond of compound [13](Cl)$_2$ is also photochemically labile, whereas it is thermally quite stable in the dark.

Example 6

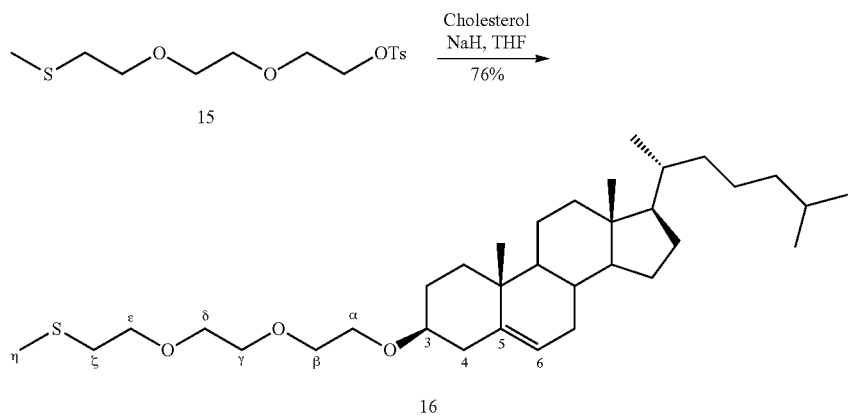

Scheme 10. Synthesis of thioester-cholesterol compound 16.

Compound 16.

A suspension of sodium hydride (0.22 g, 9.17 mmol) in dry tetrahydrofuran (40 mL) was prepared under argon. While stirring cholesterol (1.20 g, 3.10 mmol) was added to the flask. After 30 min, compound 15 (1.32 g, 3.95 mmol) in dry tetrahydrofuran (5 mL) was added to the mixture, which was then refluxed under argon for 48 h. The flask was cooled to room temperature, 60 mL a mixture of water and HCl (1 M) (50:50) was added, and the product was extracted three times with 40 mL diethylether and petroleum ether (1:15 (v/v)). The combined organic layers were washed once with 30 mL HCl (1 M), dried with MgSO$_4$, and evaporated to give compound 16 as a sticky white solid (1.31 gr, 76%). $^1$H NMR (300 MHz, δ in CDCl$_3$): 5.34 (d, J=5.1 Hz, 1H, 6), 3.74-3.57 (m, 10H, α+β+γ+δ+ε), 3.17 (m, 1H, 3), 2.69 (t, J=6.9 Hz, 2H, ζ) 2.42-2.19 (m, 2H), 2.14 (s, 3H, η), 2.05-0.81 (m, 42H), 0.67 (s, 3H). $^{13}$C NMR (75 MHz, δ in CDCl$_3$): 141.17 (C5), 121.70 (C6), 79.67 (C3), 71.58+71.13+70.81+70.51 (α+β+γ+δ), 67.48 (ε), 56.96, 56.34, 50.37, 42.49, 39.97, 39.68, 39.25, 37.42, 37.04, 36.36, 35.94, 33.61, 32.12 (ζ), 32.07, 28.54, 28.39, 28.17, 24.45, 23.99, 22.96, 22.71, 21.24, 19.54, 18.88, 16.20 (η), 12.02. High resolution ES MS m/z exp (calc): 549.43413 (549.43413, [M+H]$^+$), 566.46068 (566.45998, [M+NH$_4$]$^+$), 571.41608 (571.41482, [M+Na]$^+$). C,H,N,S expt 74.39/11.02/0.00/5.84; calc 74.39/11.16/0.0/5.85 for C$_{34}$H$_{60}$O$_3$S Example 7

Figure 5:
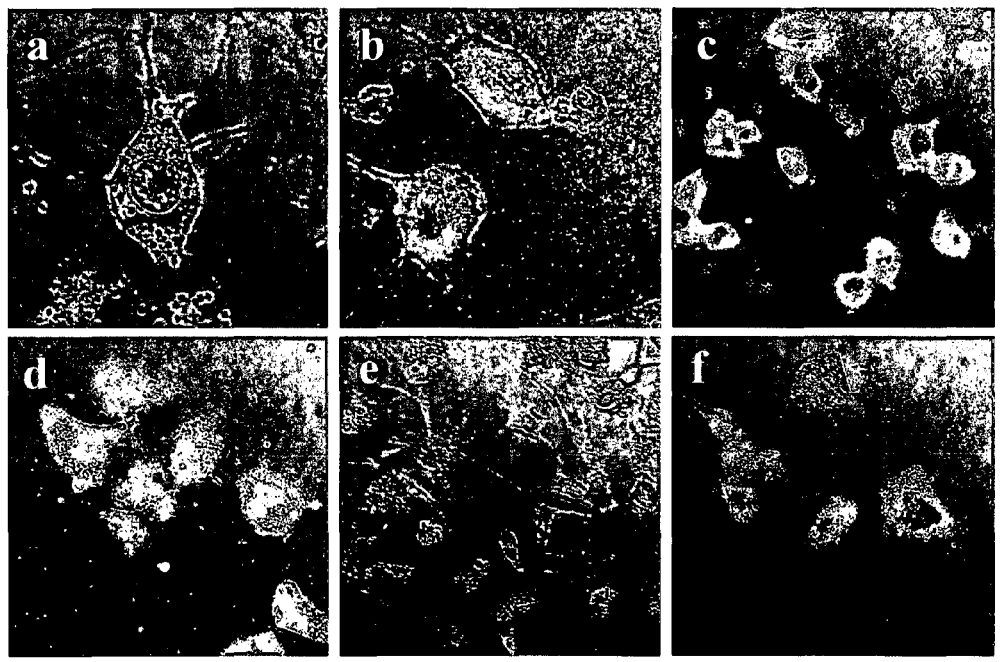
FIG. 5 shows overlays of phase contrast and fluorescence confocal microscopy pictures of HepG2 cancer cell after incubation with DMPC (a-c) and DMPG (d-f) containing 0, 5, or 10 mol % of compound $[5](PF_6)_2$, and 5 mol % of the fluorescently labeled lipid DPPC-NBD. Lipid composition of the liposomes: DMPC:DPPC-NBD:$[5](PF_6)_2$ a) 95:5:0; b) 95:5:5; and c) 95:5:10, and DMPG:DPPC-NBD:Ru—SRR' liposomes (d-e) with compositions d) 95:5:0; e) 95:5:5; and f) 95:5:10.

DMPC Liposomes are Suitable Carriers to Transport Cationic Ru Complexes into Cancer Cells Neutral dimyristoylphosphatidylcholine (DMPC) or anionic dimyristoylphosphatidylglycerol (DMPG) liposomes including 0, 5, or 10 mol % of compound [5](PF$_6$)$_2$ were prepared. The procedure was the same as in Example 1, but the liposomes also included 5 mol % of a fluorescently labelled lipid (DPPC-NBD). HepG2 cancer cells were incubated for 1 h with such liposomes at 37° C. under an atmosphere of 5% CO$_2$ and 95% air. After washing, confocal microscopy images were taken to evaluate liposome uptake. As shown in FIG. 5 there is negligible uptake of DMPC liposomes in absence of Ru (a), whereas in presence of Ru liposome uptake is excellent (b & c). On the contrary, the negatively charged DMPG liposomes without Ru are well taken up, but addition of the Ru complexes quenches fully (e) of partially (f) liposome uptake. This experiment shows that charges at the lipid bilayer surface strongly influence liposome uptake, and that cationic Ru complexes promote the uptake of neutral liposomes by cancer cells. Thus, neutral liposomes are a suitable means for transporting Ru prodrugs into cancer cells.

BIBLIOGRAPHY

1. Reedijk, J., *Platin. Met. Rev.* 2008, 52, 2.
2. Novakova, O.; Kasparova, J.; Vrana, O.; Van Vliet, P. M.; Reedijk, J.; Brabec, V., *Biochemistry* 1995, 34, 12369.
3. Hotze, A. C. G.; Bacac, M.; Velders, A. H.; Jansen, B. A. J.; Kooijman, H.; Spek, A. L.; Haasnoot, J. G.; Reedijk, J., *J. Med. Chem.* 2003, 46, 1743.
4. Corral, E.; Hotze, A. C. G.; den Dulk, H.; Leczkowska, A.; Rodger, A.; Hannon, M. J.; Reedijk, J., *J. Biol. Inorg. Chem.* 2009, 14, 439.
5. Witczak, Z.; Culhane, J., *Appl. Microbiol. Biotechnol.* 2005, 69, 237.
6. Desai, U.; Trivedi, G., *Steroids* 1991, 56, 185.
7. Sheldrick, W. S.; Exner, R., *J. Organomet. Chem.* 1990, 386, 375.
8. Collin, J.-P.; Jouvenot, D.; Koizumi, M.; Sauvage, J.-P., *Inorg. Chim. Acta* 2007, 360, 923.
9. Nikolenko, V.; Yuste, R.; Zayat, L.; Baraldo, L. M.; Etchenique, R., *Chem. Commun.* 2005, 1752.
10. Strickler, J.; Webb, W., 1991, 16, 1780.
11. Denk, W.; Strickler, J.; Webb, W., 1990, 248, 73.
12. Denk, W., 1994, 91, 6629.
13. Takeuchi, K. J.; Thompson, M. S.; Pipes, D. W.; Meyer, T. J., *Inorg. Chem.* 1984, 23, 1845.
14. Calvert, J. G.; Pitts, J. N., Chemical actinometer for the determination of ultraviolet light intensities. In *Photochemistry*, Wiley and Sons: New York, 1967; pp 780.

15. Rouser, G.; Fleische. S; Yamamoto, A., *Lipids* 1970, 5, 494.
16. Bligh, E. G.; Dyer, W. J., *Can. J. Biochem. Physiol.* 1959, 37, 911.
17. Root, M. J.; Deutsch, E., *Inorg. Chem.* 1985, 24, 1464.
18. Bonnet, S.; Collin, J.; Gruber, N.; Sauvage, J.; Schofield, E., *Dalton Trans.* 2003, 4654.
19. Jackson, A.; Davis, J.; Pither, R.; Rodger, A., *Inorg. Chem.* 2001, 40, 3964.
20. Buil, M. L.; Esteruelas, M. A.; Garces, K.; Onate, E., *Organometallics* 2009, 28, 5691.
21. Jaouen, G.; Vessieres, A.; Butler, I., *Acc. Chem. Res.* 1993, 26, 361.
22. Lo, K. K.-W.; Tsang, K. H.-K.; Sze, K.-S.; Chung, C.-K.; Lee, T. K.-M.; Zhang, K. Y.; Hui, W.-K.; Li, C.-K.; Lau, J. S.-Y.; Ng, D. C.-M.; Zhu, N., *Coord. Chem. Rev.* 2007, 251, 2292.
23. Schobert, R.; Bernhardt, G.; Biersack, B.; Bollwein, S.; Fallahi, M.; Grotemeier, A.; Hammond, G. L., *Chem. Med. Chem.* 2007, 2, 333.
24. d'Hardemare, A. D.; Torelli, S.; Serratrice, G.; Pierre, J. L., *Biometals* 2006, 19, 349.
25. Jiang, H.; Smith, B. D., *Chem. Commun.* 2006, 1407.
26. Doyle, E. L.; Hunter, C. A.; Phillips, H. C.; Webb, S. J.; Williams, N. H., *J. Am. Chem. Soc.* 2003, 125, 4593.
27. Hecker, C. R.; Fanwick, P. E.; McMillin, D. R., *Inorg. Chem.* 1991, 30, 659.
28. Laemmel, A.; Collin, J.; Sauvage, J., *Cr. Acad. Sci. Paris IIc* 2000, 3, 43.
29. Bonnet, S.; Collin, J.; Sauvage, P., *Inorg. Chem.* 2006, 45, 4024.
30. Ossipov, D.; Gohil, S.; Chattopadhyaya, J., *J. Am. Chem. Soc.* 2002, 124, 13416.
31. Schofield, E.; Collin, J.; Gruber, N.; Sauvage, J., *Chem. Commun.* 2003, 188.
32. Bonnet, S.; Collin, J.; Sauvage, J.; Schofield, E., *Inorg. Chem.* 2004, 43, 8346.
33. Sigel, H.; McCormic, D.; Griesser, R.; Prijs, B.; Wright, L., *Biochemistry* 1969, 8, 2687.

The invention claimed is:

1. A pharmaceutical composition comprising a compound having the formula R—Y, wherein R is a ruthenium complex and Y is at least one sulphur-containing photoreleasable group, and wherein the compound comprises at least one ruthenium-sulphur bond; or a pharmaceutically acceptable salt, solvate, ester or amide, together with a pharmaceutically acceptable carrier, such that upon influence of visible or near infra-red light (400-1400 nm) in vivo, said at least one ruthenium-sulphur bond is broken, thereby generating a pharmacologically active compound.

2. The composition according to claim 1 wherein the photoreleasable group Y is a sulfur-containing monodentate or bidentate ligand capable of coordinating to the Ru complex through at least one sulfur atom.

3. The composition according to claim 2 wherein the sulfur-containing photoreleasable groups are thioethers capable of coordinating to the Ru complex through at least one sulfur atom.

4. The composition according to claim 3 wherein the thioether groups which are capable of forming at least one coordination bond(s) to the Ru complex are selected from compounds based on biotin, alkylcysteine, methionine, alkylated thiols, dimethylsulfide, phenylmethylsulfide, diphenylsulfide, dialkylsulfide, phenothiazine, or the thioether-based ligand is a methionine- or alkylcystein-containing polypeptide, or a thioether-containing organic molecule derived from a natural compound, ranitidine, methyl coenzyme M, a thio-ether-containing sugar, a thioether-containing steroid, a thioether-containing beta lactam antibiotic, a thio-analogue of an oxygen-based ether, or the thioether group which is part of a peptide, protein, antibody or antibody fragment, capable of targeting a diseased cell.

5. The composition according to claim 1 wherein the sulphur containing photoreleasable groups are conjugated, bonded or otherwise associated with a lipid, or cholesterol.

6. The composition according to claim 5 wherein the lipid, or cholesterol is part of a drug delivery system.

7. The composition according to claim 6 wherein the drug delivery system further comprises other elements having a therapeutic or pharmacological function, which are designed to specifically bind and/or target a diseased cell, or one or more sterically stabilizing groups for prolonging in vivo circulation times.

8. The composition according to claim 1 wherein the Ru complex has one of the following structures:

A]

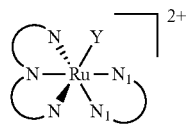

$[Ru(N-N-N)(N_1-N_1)(Y)]^{2+}$

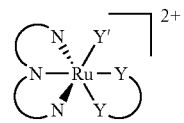

$[Ru(N-N-N)(Y-Y)(Y')]^{2+}$

B]

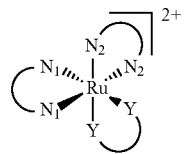

$[Ru(N_1-N_1)(N_2-N_2)(Y-Y)]^{2+}$

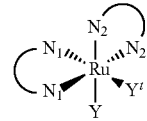

$[Ru(N_1-N_1)(N_2-N_2)(Y)(Y')]^{2+}$

C]

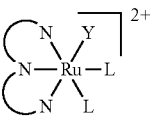

$[Ru(N-N-N)(L)_2(Y)]^{2+}$

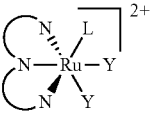

$[Ru(N-N-N)(Y)_2(L)]^{2+}$

-continued

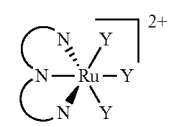

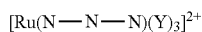

wherein, in complexes of group A and B, Y and Y' can be the same or different monodentate sulfur-containing ligands as defined in claim 4 that can be photoreleased, whereas the terdentate (N—N—N) or bidentate ($N_1$—$N_1$, N2-N2) chelates stay bound to ruthenium;

optionally Y and/or Y' is covalently bound to a lipid, or cholesterol moiety and cleavage of the ruthenium-sulfur bond induces the detachment of the ruthenium complex from the lipid, or cholesterol or cholesterol derivative moiety; Y—Y is a sulfur-containing bidentate ligand that can be photoreleased and is optionally covalently bound to a lipid, or cholesterol moiety, and $N_1$—$N_1$ and $N_2$—$N_2$ are selected from one or more of the following structures:

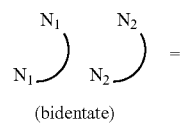
(bidentate)

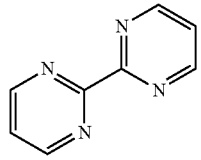

bpy

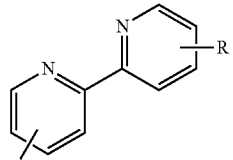

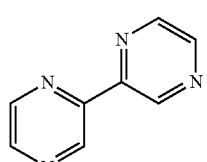

dmbpy

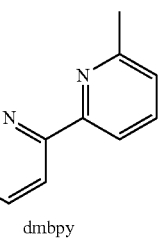

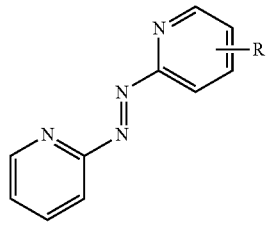

apy

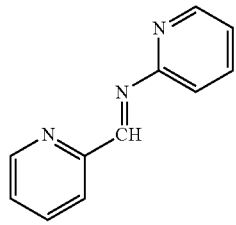

pyridylimine

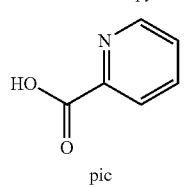

pic

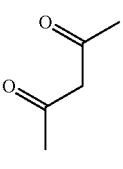

acac

-continued

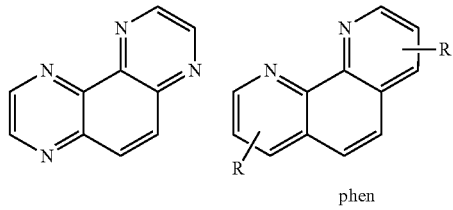

phen

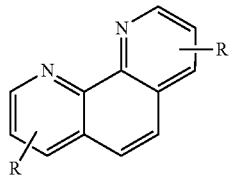

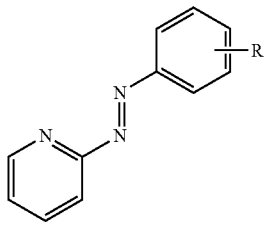

azpy

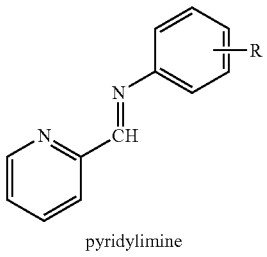

pyridylimine

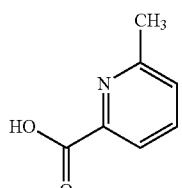

Me-pic

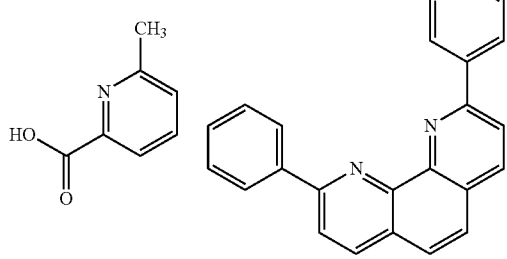

dip

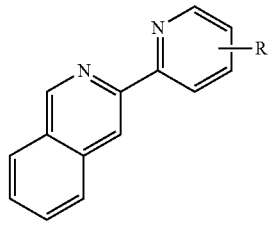

dmp

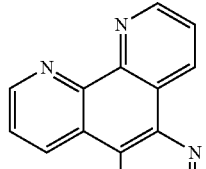

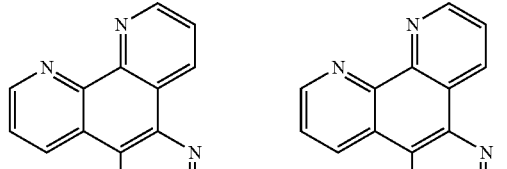

dppn     dppz

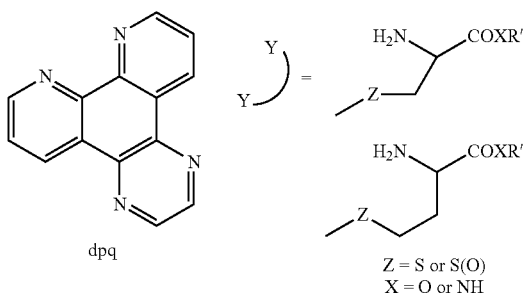

dpq $Z = S \text{ or } S(O)$
$X = O \text{ or } NH$

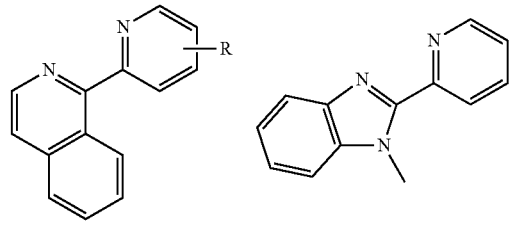

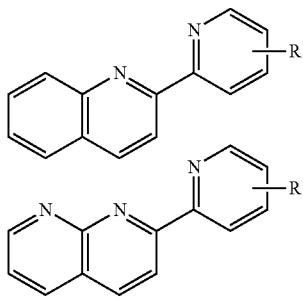

where R is a hydroxy, H, $C_1$-$C_4$ alkyl, carboxy, alkoxy, amino, N,N-dimethylamino, carbonyl, halide, or nitro group; or Y' is a monodentate ligand that is photochemically less labile than Y; and in group C, N—N—N is a terdentate chelate that stays bound to ruthenium (where R is a hydroxy, H, $C_1$-$C_4$ alkyl, carboxy, alkoxy, amino, N,N-dimethylamino, carbonyl, halide, or nitro group, and R' is H or an alkyl group).

9. The composition according to claim 1 wherein the Ru complex conforms to one of the following structures;

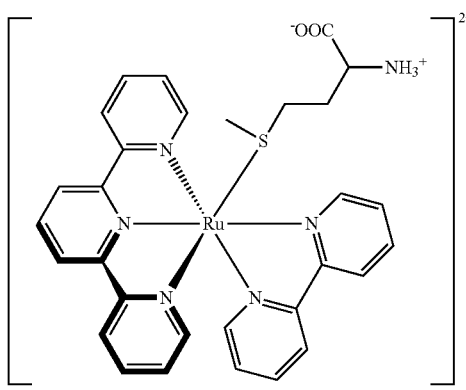

[Ru(terpy)(bpy)(methionine)]$^{2+}$

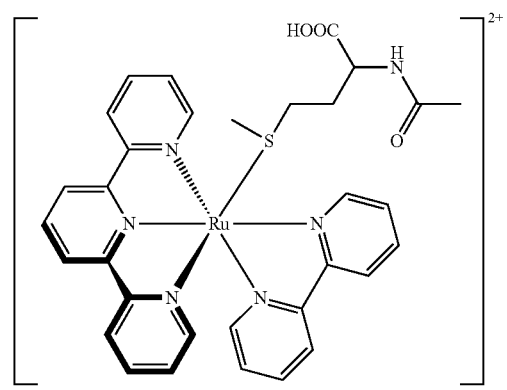

[Ru(terpy)(bpy)(AMet)]$^{2+}$

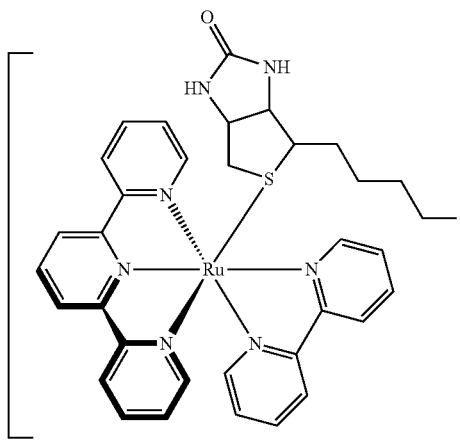

[Ru(terpy)(bpy)(biotin)]$^{2+}$

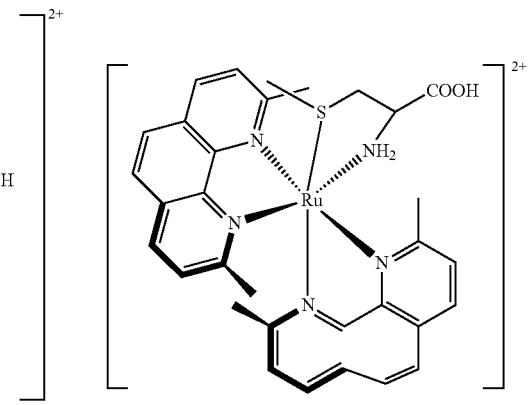

α-[Ru(dmp)$_2$(Met-cystein)]$^{2+}$

-continued
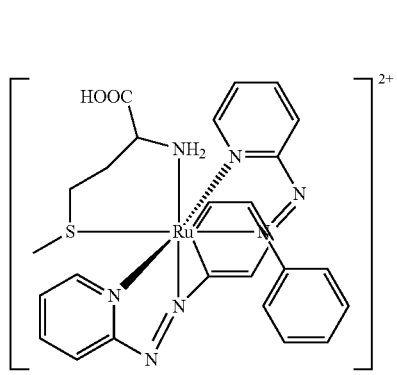
α-[Ru(azpy)₂(methionine)]²⁺
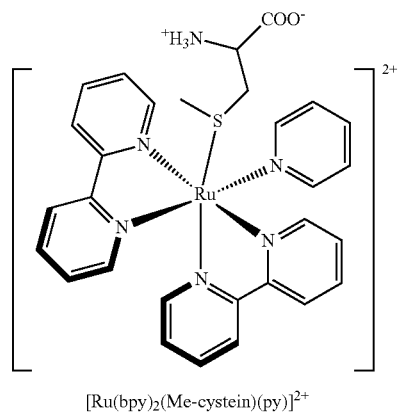
[Ru(bpy)₂(Me-cystein)(py)]²⁺
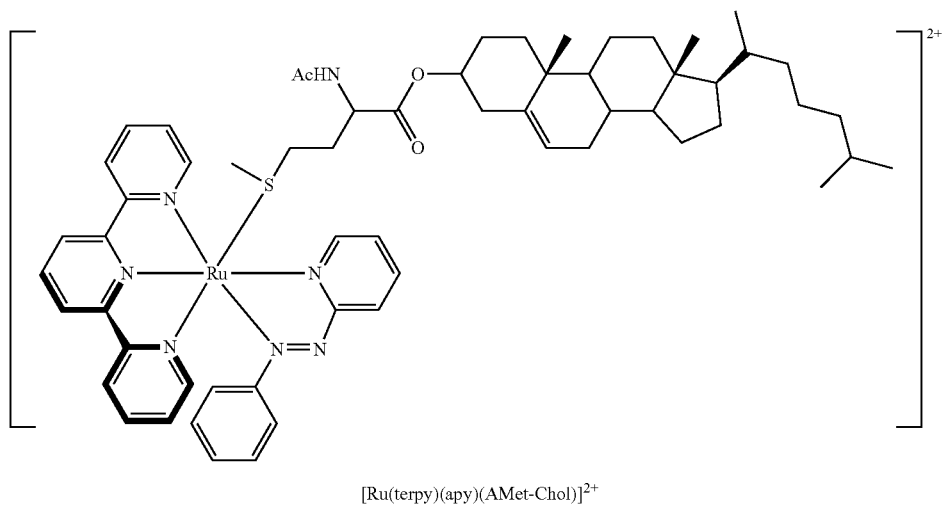
[Ru(terpy)(apy)(AMet-Chol)]²⁺
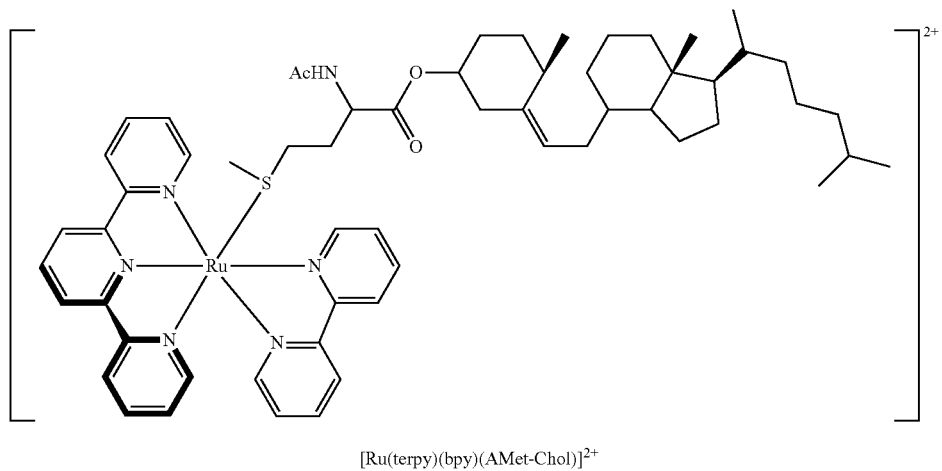
[Ru(terpy)(bpy)(AMet-Chol)]²⁺

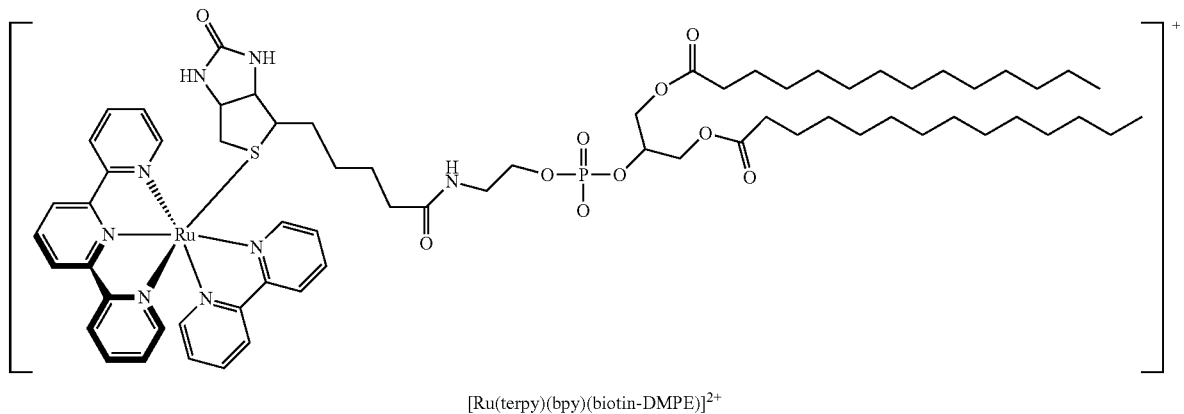

[Ru(terpy)(bpy)(biotin-DMPE)]$^{2+}$

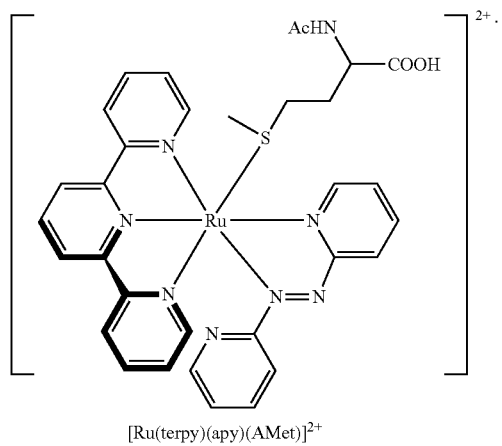

[Ru(terpy)(apy)(AMet)]$^{2+}$

10. The composition according to claim 1, wherein the composition is effective as a cytotoxic, anti-microbial, anti-viral, anti-inflammatory, anti-diabetic, cardiovascular, anti-psychotic, analgesic, anti-rheumatics, anti-autoimmune, anti-neurodegenerative, anti-toxin, steroidal, hormonal or wound-healing.

11. A method of treating conditions associated with abnormal proliferation of cells, and cancers, hyperproliferative disorders, rheumatoid/autoimmune conditions, sickle cell anemia and thalasemias, comprising administering to a subject in need thereof a therapeutically useful amount of a compound having the formula R—Y, wherein R is a ruthenium complex and Y is at least one sulphur-containing photoreleasable group, and wherein the compound comprises at least one ruthenium-sulphur bond; or a pharmaceutically acceptable salt, solvate, ester or amide; and irradiating the compound with visible or near infra-red light (400-1400 nm) in order to cleave one or more ruthenium-sulphur bonds and release a pharmacologically active ruthenium compound.

12. A method of treatment of a disease involving cell proliferation, comprising administering a therapeutically useful amount of a composition according to claim 1, to a subject in need thereof and irradiating the compound with visible or near infra-red light in order to cleave one or more Ru-S bonds and release a pharmacologically active ruthenium compound.

13. The composition according to claim 1 wherein the compound is provided in an aqueous solution.

14. The composition according to claim 1 provided in a dark container or receptacle prior to use or application of the composition.

15. The composition according to claim 8, wherein group C is selected from:

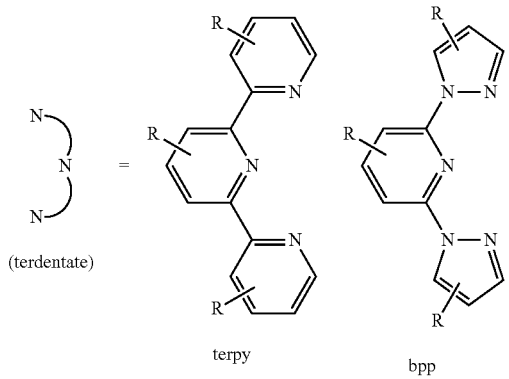

-continued
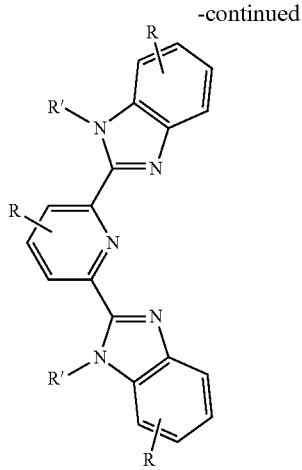
Mebimpy
wherein Y is a monodentate sulfur-based ligand as defined in claim 4 that can be photoreleased optionally covalently bound to a lipid or cholesterol moiety and each L is the same or different monodentate ligand that is photochemically less labile than Y.
* * * * *